United States Patent
Najafi et al.

(10) Patent No.: US 12,400,410 B2
(45) Date of Patent: Aug. 26, 2025

(54) SYSTEM AND METHOD FOR GENERATING AND VISUALIZING VIRTUAL FIGURES FROM PRESSURE DATA CAPTURED USING WEIGHT SUPPORT DEVICES FOR VISUALIZATION OF USER MOVEMENT

(71) Applicant: XSENSOR Technology Corporation, SE Calgary (CA)

(72) Inventors: Mohammad Najafi, Calgary (CA); Ian Main, Calgary (CA); Terence Russell, Calgary (CA); Michael Reid Ivey, Calgary (CA); Alexander Wong, Waterloo (CA)

(73) Assignee: XSENSOR Technology Corporation, Calgary (CA)

( * ) Notice: Subject to any disclaimer, the term of this patent is extended or adjusted under 35 U.S.C. 154(b) by 0 days.

(21) Appl. No.: 17/975,405

(22) Filed: Oct. 27, 2022

(65) Prior Publication Data
US 2023/0137904 A1     May 4, 2023

Related U.S. Application Data

(60) Provisional application No. 63/273,015, filed on Oct. 28, 2021.

(51) Int. Cl.
*G06T 19/20*     (2011.01)
*A61B 5/00*     (2006.01)
(Continued)

(52) U.S. Cl.
CPC ............ *G06T 19/20* (2013.01); *A61B 5/6892* (2013.01); *A61B 5/7275* (2013.01); *A61B 5/744* (2013.01);
(Continued)

(58) Field of Classification Search
CPC ......... G06T 19/006; G06T 2207/20081; G06T 2207/30196; G06T 13/40; G06T 19/20;
(Continued)

(56) References Cited

U.S. PATENT DOCUMENTS 2,378,039 A    6/1945   Schenker
2,804,129 A    8/1957   Propst
(Continued)

FOREIGN PATENT DOCUMENTS

AU          48619/93      5/1994
AU          649391 B3    5/1994
(Continued)

OTHER PUBLICATIONS

A Good Mattress is a Dream Come True, New York Times News Service, Mar. 29, 1998, 1 page, available at http://articles.chicagotribune.com/1998-03-29/news/9803290437.sub.--1.sub-.--mattress-sleep-wake-disorder-center-bed.
(Continued)

*Primary Examiner* — Chante E Harrison
(74) *Attorney, Agent, or Firm* — Fenwick & West LLP

(57) ABSTRACT

A weight support device includes a sensor grid that measures pressure data while a user is on the weight support device. The weight support device is connected to a computer that analyzes the pressure data and generates a virtual figure to represent the user. Based on the pressure data, the computer determines how the user moves and adjusts relative positions of segments in the virtual figure that represent various body parts corresponding to the movements of the user. The relative positions of the segments may be determined based on a kinematic model. The virtual figure is presented on a display (e.g., in a video) to illustrate how the user moved.

20 Claims, 20 Drawing Sheets

(51) Int. Cl.
*G06N 5/022* (2023.01)
*G06T 7/73* (2017.01)
*G06T 13/40* (2011.01)
*G01L 1/14* (2006.01)

(52) U.S. Cl.
CPC .............. *G06N 5/022* (2013.01); *G06T 7/75* (2017.01); *G06T 13/40* (2013.01); *A61B 2562/0247* (2013.01); *A61B 2562/046* (2013.01); *G01L 1/146* (2013.01); *G06T 2207/10016* (2013.01); *G06T 2207/20081* (2013.01); *G06T 2207/30196* (2013.01); *G06T 2210/41* (2013.01); *G06T 2219/2004* (2013.01)

(58) Field of Classification Search
CPC .......... G06T 2200/24; A61B 2562/046; A61B 2562/0247; A61B 5/11; A61B 5/103; A61B 5/445; A61B 5/743; A61B 5/744; A61B 5/6843; A61B 5/7275; A61B 5/447; A61B 5/1114; A61B 5/1115; A61B 5/1116; A61B 5/4815; G16H 50/00; G16H 50/20
See application file for complete search history.

(56) References Cited

U.S. PATENT DOCUMENTS

| | | |
|---|---|---|
| 2,976,725 A | 3/1961 | Byer |
| 3,100,992 A | 8/1963 | Davis |
| 3,195,347 A | 7/1965 | Janapol |
| 3,334,517 A | 8/1967 | Janapol |
| 3,413,849 A | 12/1968 | Janapol |
| 3,565,195 A | 2/1971 | Miller et al. |
| 3,826,926 A | 7/1974 | White et al. |
| 3,875,481 A | 4/1975 | Miller et al. |
| 4,005,438 A | 1/1977 | Meltzer et al. |
| 4,134,063 A | 1/1979 | Nicol et al. |
| 4,266,263 A | 5/1981 | Haberl et al. |
| 4,370,697 A | 1/1983 | Haberl et al. |
| 4,554,930 A | 11/1985 | Kress |
| 4,584,625 A | 4/1986 | Kellogg |
| 4,662,012 A | 5/1987 | Torbet |
| 4,827,763 A | 5/1989 | Bourland et al. |
| 4,986,136 A | 1/1991 | Brunner et al. |
| 5,010,772 A | 4/1991 | Bourland et al. |
| 5,148,706 A | 9/1992 | Masuda et al. |
| 5,231,717 A | 8/1993 | Scott et al. |
| 5,306,912 A | 4/1994 | Sibbald et al. |
| 5,401,922 A | 3/1995 | Asta |
| 5,447,076 A | 9/1995 | Ziegler |
| 5,487,196 A | 1/1996 | Wilkinson et al. |
| 5,514,832 A | 5/1996 | Dusablon et al. |
| 5,653,939 A | 8/1997 | Hollis et al. |
| 5,693,886 A | 12/1997 | Seimiya et al. |
| 5,745,940 A | 5/1998 | Roberts et al. |
| 5,815,865 A | 10/1998 | Washburn et al. |
| 5,848,450 A | 12/1998 | Oexman et al. |
| 5,963,997 A | 10/1999 | Hagopian |
| 5,970,789 A | 10/1999 | Meyer et al. |
| 5,993,400 A | 11/1999 | Rincoe et al. |
| 6,192,538 B1 | 2/2001 | Fogel |
| 6,280,392 B1 | 8/2001 | Yoshimi et al. |
| 6,585,328 B1 | 7/2003 | Oexman et al. |
| 6,826,968 B2 | 12/2004 | Manaresi et al. |
| 7,067,979 B2 | 6/2006 | Sakamoto |
| 7,107,642 B2 | 9/2006 | Wong et al. |
| 7,378,975 B1 | 5/2008 | Smith et al. |
| 7,467,058 B2 | 12/2008 | Boyd |
| 7,580,030 B2 | 8/2009 | Marten |
| 7,609,178 B2 | 10/2009 | Son et al. |
| 7,638,350 B2 | 12/2009 | Deconde et al. |
| 7,937,239 B2 | 5/2011 | Boyd |
| 8,011,041 B2 | 9/2011 | Hann |
| 8,121,800 B2 | 2/2012 | Altman et al. |
| 8,272,276 B2 | 9/2012 | Gorjanc et al. |
| 8,458,042 B1 | 6/2013 | Roberts et al. |
| 8,463,006 B2 | 6/2013 | Prokoski |
| 8,544,336 B2 | 10/2013 | Main et al. |
| 8,893,561 B2 | 11/2014 | Gorjanc et al. |
| 9,186,479 B1 | 11/2015 | Franceschetti et al. |
| 9,320,665 B2 | 4/2016 | Main et al. |
| 9,659,322 B2 | 5/2017 | Gorjanc et al. |
| 9,848,712 B2 | 12/2017 | Main et al. |
| 9,860,982 B1 | 1/2018 | Main et al. |
| 10,314,407 B1 | 6/2019 | Main et al. |
| 10,562,412 B1 | 2/2020 | Main et al. |
| 10,729,876 B2 | 8/2020 | Main et al. |
| 10,973,344 B2 | 4/2021 | Poodeh et al. |
| 11,911,660 B2 * | 2/2024 | Bentley ................ G01P 13/00 |
| 2002/0155728 A1 | 10/2002 | Khandros et al. |
| 2002/0184711 A1 | 12/2002 | Mahoney et al. |
| 2003/0121101 A1 | 7/2003 | Corzani et al. |
| 2004/0133092 A1 | 7/2004 | Kain |
| 2005/0165284 A1 | 7/2005 | Gefen |
| 2005/0173144 A1 | 8/2005 | Federighi et al. |
| 2005/0241409 A1 | 11/2005 | Taylor |
| 2007/0069642 A1 | 3/2007 | Kitai et al. |
| 2007/0257821 A1 | 11/2007 | Son et al. |
| 2008/0052837 A1 | 3/2008 | Blumberg |
| 2008/0062176 A1 | 3/2008 | Arya |
| 2008/0180390 A1 | 7/2008 | Yoshikawa |
| 2008/0201856 A1 | 8/2008 | Howard |
| 2008/0275349 A1 | 11/2008 | Halperin et al. |
| 2009/0062693 A1 | 3/2009 | Woolfson et al. |
| 2009/0070939 A1 | 3/2009 | Hann |
| 2009/0093717 A1 | 4/2009 | Carneiro et al. |
| 2009/0209830 A1 | 8/2009 | Nagle et al. |
| 2009/0216466 A1 | 8/2009 | Altman et al. |
| 2009/0240514 A1 | 9/2009 | Oexman et al. |
| 2010/0022850 A1 | 1/2010 | Mc Kenna et al. |
| 2010/0174198 A1 | 7/2010 | Young et al. |
| 2010/0191541 A1 | 7/2010 | Prokoski |
| 2010/0317930 A1 | 12/2010 | Oexman et al. |
| 2010/0318239 A1 | 12/2010 | Oexman et al. |
| 2011/0010014 A1 | 1/2011 | Oexman et al. |
| 2011/0112442 A1 | 5/2011 | Meger et al. |
| 2011/0245732 A1 | 10/2011 | Mravyan et al. |
| 2011/0308019 A1 | 12/2011 | Terawaki et al. |
| 2012/0296156 A1 | 11/2012 | Auphan |
| 2012/0311790 A1 | 12/2012 | Nomura et al. |
| 2013/0000047 A1 | 1/2013 | McCann et al. |
| 2013/0006151 A1 | 1/2013 | Main et al. |
| 2013/0090571 A1 * | 4/2013 | Nourani ................ G16H 50/20 |
| | | 600/587 |
| 2013/0144751 A1 | 6/2013 | Gorjanc et al. |
| 2013/0283530 A1 | 10/2013 | Main et al. |
| 2014/0343889 A1 | 11/2014 | Ben Shalom et al. |
| 2014/0366277 A1 | 12/2014 | Niederkrom et al. |
| 2015/0320352 A1 * | 11/2015 | Ben Shalom ........ A61B 5/6892 |
| | | 600/587 |
| 2015/0371522 A1 | 12/2015 | Mravyan et al. |
| 2017/0281073 A1 | 10/2017 | Drennan et al. |
| 2018/0027988 A1 | 2/2018 | Poodeh et al. |
| 2018/0064402 A1 | 3/2018 | Leydon |
| 2019/0026957 A1 | 1/2019 | Gausebeck |
| 2019/0053761 A1 * | 2/2019 | Young .................. A61B 5/1102 |
| 2019/0307405 A1 * | 10/2019 | Terry .................... G16H 10/60 |
| 2020/0405217 A1 | 12/2020 | Jayaraman et al. |
| 2021/0196055 A1 | 7/2021 | Poodeh et al. |
| 2022/0079514 A1 | 3/2022 | Main et al. |
| 2022/0087617 A1 | 3/2022 | Main et al. |
| 2023/0011717 A1 * | 1/2023 | Larson ................ A61B 5/6823 |
| 2024/0225481 A1 * | 7/2024 | Smith .................... G16H 40/63 |

FOREIGN PATENT DOCUMENTS

| | | | |
|---|---|---|---|
| CN | 101803983 A | | 8/2010 |
| CN | 106264447 A | * | 1/2017 |
| CN | 108289638 A | * | 7/2018 .............. A61B 5/00 |
| CN | 112151172 A | * | 12/2020 .......... A61B 5/1117 |
| CN | 115291533 A | * | 11/2022 |
| CN | 116098417 A | * | 5/2023 |
| CN | 116115973 A | * | 5/2023 |

(56) References Cited

FOREIGN PATENT DOCUMENTS

| | | | |
|---|---|---|---|
| EP | 2182339 A1 | 5/2010 | |
| FR | 2720622 A1 | 12/1995 | |
| JP | H04-325116 | 11/1992 | |
| JP | 2009-119082 A | 6/2009 | |
| WO | WO 01/00089 A1 | 1/2001 | |
| WO | WO 2009/102361 A1 | 8/2009 | |
| WO | WO 2010/045741 A1 | 4/2010 | |
| WO | WO 2011/066151 A1 | 6/2011 | |
| WO | WO 2011/091517 A1 | 8/2011 | |
| WO | WO 2012/160502 A1 | 11/2012 | |
| WO | WO 2013/085785 A1 | 6/2013 | |
| WO | WO 2014/145436 A1 | 9/2014 | |
| WO | WO-2018085510 A1 * | 5/2018 | ............. A61B 5/002 |

OTHER PUBLICATIONS

Amazon.com, "Honeywell Home RCHW3610WF1006/N Water Leak Detector," Apr. 20, 2018, nine pages, [Online] [Retrieved on Aug. 31, 2021] Retrieved from the Internet <URL: https://www.amazon.ca/Honeywell-RCHW3610WF1006-Water-Leak-Detector/dp/B07CJG91DM/ref=asc_df_B07CJG91DM/?tag=googleshopc0c-20&linkCode=df0&hvadid=292938317460&hvpos=&hvnetw=g&hvrand=9101712106439063987&hvpone=&hvptwo=&hvqmt=&hvdev=c&hvdvcmdl=&hvlocint=&hvlocphy=9001314&hvtargid=pla-554077522699&psc=1>.

Barhyte, et al., Selection of a Standard Hospital Mattress: Data-Based Decision Making, vol. 22, No. 6 Journal of Wound Ostomy & Continence Nursing, Nov. 1995, pp. 267-270, vol. 22, No. 6.

Bates-Jensen, B. M. et al., "Subepidermal Moisture Detection of Pressure Induced Tissue Damage on the Trunk: The Pressure Ulcer Detection (PUD) Study Outcomes," Wound Repair Regen, 25(3), May 31, 2017, pp. 502-511.

Brienza, et al., A Method for Custom-Contoured Cushion Design Using Interface Pressure Measurements, IEEE Transactions on Rehabilitation Engineering, Mar. 1999, pp. 99-108, vol. 7, No. 1.

Brienza, et al., Seat Cushion Optimization: a Comparison of Interface Pressure and Tissue Stiffness Characteristics for Spinal Cord Injured and Elderly Patients, vol. 79, Archives of Physical Medicine & Rehabilitation, Apr. 1998, pp. 388-394, vol. 79.

Chiradejnant, A., The Study of the Reliability and Validity of the Ergocheck Measurement System, School of Physiotherapy, University of South Australia, 1998. 74 pages.

Clark, M., "Comparison of the Pressure Redistributing Attributes of a Selection of Bed Mattresses Used to Prevent Pressure Sores," The Journal of Tissue Viability, Jul. 1991, pp. 65-67, vol. 1 No. 3.

Cork, Russel, "XSENSOR technology: A pressure imaging overview ", Published in Sensor Review on 27.1 (2007): 24.; extracted for PQ dialog search on May 11, 2015.

Defloor, T. et al., "Sitting Posture and Prevention of Pressure Ulcers," Applied Nursing Research, Aug. 1999, pp. 137-142, vol. 12 No. 3.

Digi-Key, "Water Contact Indicator Tape," Date Unknown, three pages, [Online] [Retrieved on Aug. 31, 2021] Retrieved from the Internet <URL: https://www.digikey.ca/en/product-highlight/3/3m-tc/water-contact-indicator-tape>.

Ergocheck Brochure: Ergocheck Fulfils One of the Essential Demands of the Bedding Trade, ABW, 1994, 3 pages.

Ergocheck Measuring System, 1994 Ergocheck v.2.0 Reference Manual, 105 pages.

"Force Sensing Array Version 3.1 User Manual," 2 ed., Vista Medical Ltd., 1996, 66 pages.

Fronczek, R., et al., "Manipulation of Core Body and Skin Temperature Improves Vigilance and Maintenance of Wakefulness in Narcolepsy, " Sleep, 2008, pp. 233-240, vol. 31, No. 2.

Gignac, Tamara; "Xsensor's body maps guide manufacturers: Pressure-point technology has manyapplications"; [Final Edition] Publication info: Calgary Herald [Calgary, Alta] Mar. 13, 2006: B8.

Harstall, C., "Interface Pressure Measurement Systems for Management of Pressure Sores," Alberta Heritage Foundation for Medical Research, Sep. 1996, 21 pages.

Kreutz, D., Computerized Pressure Mapping, Advance for Directors in Rehabilitation, Nov. 11-12, 1997, 3 pages.

Krouskop, T.A. et al., "Factors Affecting the Pressure-Distributing Properties of Foam Mattress Overlays," Journal of Rehabilitation Research and Development, Jul. 1986, pp. 33-39, vol. 23, No. 3.

Lipka, D., "An Overview of Pressure-Mapping System," Technology Special Interest Section Quarterly, Dec. 1997, pp. 1-6, vol. 7 No. 4.

Machiel Van Der Loos, H.F. et al., "Development of Sensate and Robotic Bed Technologies for Vital Signs Monitoring and Sleep Quality Improvement," Autonomous Robots, 2003, pp. 67-79, vol. 15.

Malacaria, C., A Thin, Flexible, Matrix-Based Pressure Sensor, Sensors Magazine, Sep. 1998, 5 pages.

Malakuti, K., "Towards an Intelligent Bed Sensor: Non-Intrusive Monitoring of Sleep Disturbances via Computer Vision Techniques," Thesis, University of Victoria, 2008, 93 pages.

Nicol, K. et al., "Pressure Distribution on Mattresses," Journal of Biomechanics, 1993, pp. 1479-1486, vol. 26, No. 12.

Oxford Pressure Monitor, Operating Instructions (received by the Food and Drug Administration on Dec. 9, 1991), 32 pages.

Park, S.J. et al., "Measurement and Analysis of Pressure Distribution on the Bed," Proceedings of the Human Factors and Ergonomics Society 39.sup.th Annual Meeting, 1995, pp. 297-300.

PCT International Search Report and Written Opinion, PCT Application No. PCT/IB2021/000598, Feb. 18, 2022, 14 pages.

PCT Invitation to Pay Additional Fees, PCT Application No. PCT/IB2021/000598, Jan. 5, 2022, two pages.

Raymann, R., et al., "Skin deep: enhanced sleep depth by cutaneous temperature manipulation," Brain, 2008, pp. 500-513, vol. 131.

Reswick, J.B. et al., Experience at Rancho Los Amigos Hospital with Devices and Techniques to Prevent Pressure Sores, in Bedsore Biomechanics 301, 307-08 (University Park Press 1976).

Reynolds, A. et al., Pressure-Reducing Capability of Conforma II Mattress Overlay, Advances in Wound Care, Jul. 1994, pp. 36-40, vol. 7, No. 4.

Rithalia, S. V.S. et al., "Assessment of Alternating Air Mattresses Using a Time-Based Interface Pressure Threshold Technique," Journal of Rehabilitation Research and Development, Jun. 1998, pp. 225-230, vol. 35 No. 2.

Shelton, et al., Full-Body Interface Pressure Testing as a Method for Performance Evaluation of Clinical Support Surfaces, Applied Ergonomics, 1998, pp. 491-497, vol. 29, No. 6.

Sparkfun, "SparkFun Soil Moisture Sensor," Date Unknown, nine pages, [Online] [Retrieved on Aug. 31, 2021] Retrieved from the Internet <URL: https://www.sparkfun.com/products/13322>.

Talley Pressure Monitor 3, Operating Manual 1st Ed. Preliminary (received by the Food and Drug Administration on Dec. 9, 1991), 44 pages.

Telefax from A. Ahrens to L. Larson, Mar. 14, 1995, 1 page.

The Canadian Patient Safety Institute, "Never Events for Hospital Care in Canada," Sep. 2015, 11 pages, [Online] [Retrieved on Aug. 31, 2021] Retrieved from the Internet <URL: https://www.patientsafetyinstitute.ca/en/toolsResources/NeverEvents/Documents/Never Events for Hospital Care in Canada.pdf>.

U.S. Appl. No. 17/019,090, filed Feb. 3, 2023, 10 pages.

Yousefi, R. et al., "A Smart Bed Platform for Monitoring & Ulcer Prevention," 2011 4.sup.th International Conference on Biomedical Engineering and Informatics (BMEI), IEEE, 2011, pp. 1362-1366.

Yousefi, R. et al., "Bed Posture Classification for Pressure Ulcer Prevention," 2011 Annual International Conference of the IEEE, Engineering in Medicine and Biology Society, EMBC, Aug. 30, 2011-Sep. 3, 2011, pp. 7175-7178.

Zabel, M., "Buying Mattresses for Comfort," University of Minnesota, 1969, 15 pages.

* cited by examiner

SYSTEM AND METHOD FOR GENERATING AND VISUALIZING VIRTUAL FIGURES FROM PRESSURE DATA CAPTURED USING WEIGHT SUPPORT DEVICES FOR VISUALIZATION OF USER MOVEMENT

CROSS-REFERENCE TO RELATED APPLICATION

The present application claims the benefit of U.S. Provisional Patent Application 63/273,015, filed on Oct. 28, 2021, which is hereby incorporated by reference in its entirety.

TECHNICAL FIELD

The present disclosure generally relates to a weight support device including a sensor grid that can detect pressure data, and more specifically to systems and methods for generating and visualizing a virtual figure to represent a user supported by the weight support device based on the pressure data captured by the device.

BACKGROUND

Monitoring a person's movements while the user is sleeping can provide useful health information. For example, the person's movements can be used to predict pressure injuries (e.g., bedsores, pressure ulcers), predict whether the user is likely to fall from bed, determine sleep quality, adjust sleeping conditions (e.g., change bed settings, adjust room temperature), and detect seizures. To determine ways of improving the person's health, a video of the user can be recorded while the user is sleeping and reviewed using computer vision to determine how the user moved throughout the night. However, collecting, storing, and analyzing a video captured over a long period (e.g., 8 hours each night) requires a large amount of memory, time, and computational power.

SUMMARY

Embodiments disclosed relate to generating and visualizing a virtual figure representing a user of a weight support device based on pressure data captured by the device to visually illustrate movements of the user during a measurement period without collecting image data.

In one aspect, the present system may comprise of a weight support device, a side prediction engine module, a joint location prediction engine module, a kinematic engine module, and a figure generation engine module. As used herein, a module may be implemented in software executable by a processor, in hardware or a combination thereof.

In an embodiment, a continuous collection of pressure data from the weight support device during the measurement period is fed into a side prediction engine module to predict the side of the user that is in contact with the weight support device at various timestamps during the measurement period. A continuous collection of pressure data from the weight support device during the measurement period is also fed into a joint location prediction engine module to predict locations of the user's joints (e.g., knee joint, hip joint, elbow joint) at various timestamps during the measurement period. The side predictions and joint predictions are provided as input to a kinematic engine module that determines how the user moved between timestamps given motion constraints of the different types of joints. The figure generation engine module generates a virtual figure representative of the user. The movement of the user during the measurement period is illustrated by adjusting the relative positions of a head representation, a torso representation, and one or more limb representations of the virtual figure to mirror the movement of the user during the measurement period.

In another embodiment, a continuous collection of pressure data from the weight support device during the measurement period is fed directly into a figure generation engine module which analysis the data directly, with a machine learning model or an alternative processing mechanism, and generates a virtual figure representative of the user.

In some embodiments, the modules of the present system generating and visualizing a virtual figure to represent a user supported by the weight support device based on the pressure data captured by the device may be embodied in software, or in hardware in the form of an integrated circuit chip, a digital signal processor chip, or on a computer, or a combination thereof.

In this respect, before explaining at least one embodiment of the invention in detail, it is to be understood that the invention is not limited in its application to the details of construction and to the arrangements of the components set forth in the following description or the examples provided therein, or illustrated in the drawings. Therefore, it will be appreciated that a number of variants and modifications can be made without departing from the teachings of the disclosure as a whole. Therefore, the present system, method and apparatus is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

As noted above, the present disclosure relates generally to a weight support device including a sensor grid that can detect pressure data, and more specifically to systems and methods for in particular to producing generating and visualizing a virtual figure, which may be but not limited to a three-dimensional (3D) figure or a two-dimensional (2D) figure to represent a user supported by the weight support device based on the pressure data captured by the device.

The present system and method will be better understood, and objects of the invention will become apparent, when consideration is given to the following detailed description thereof. Such description makes reference to the annexed drawings, wherein.

Figure 1:
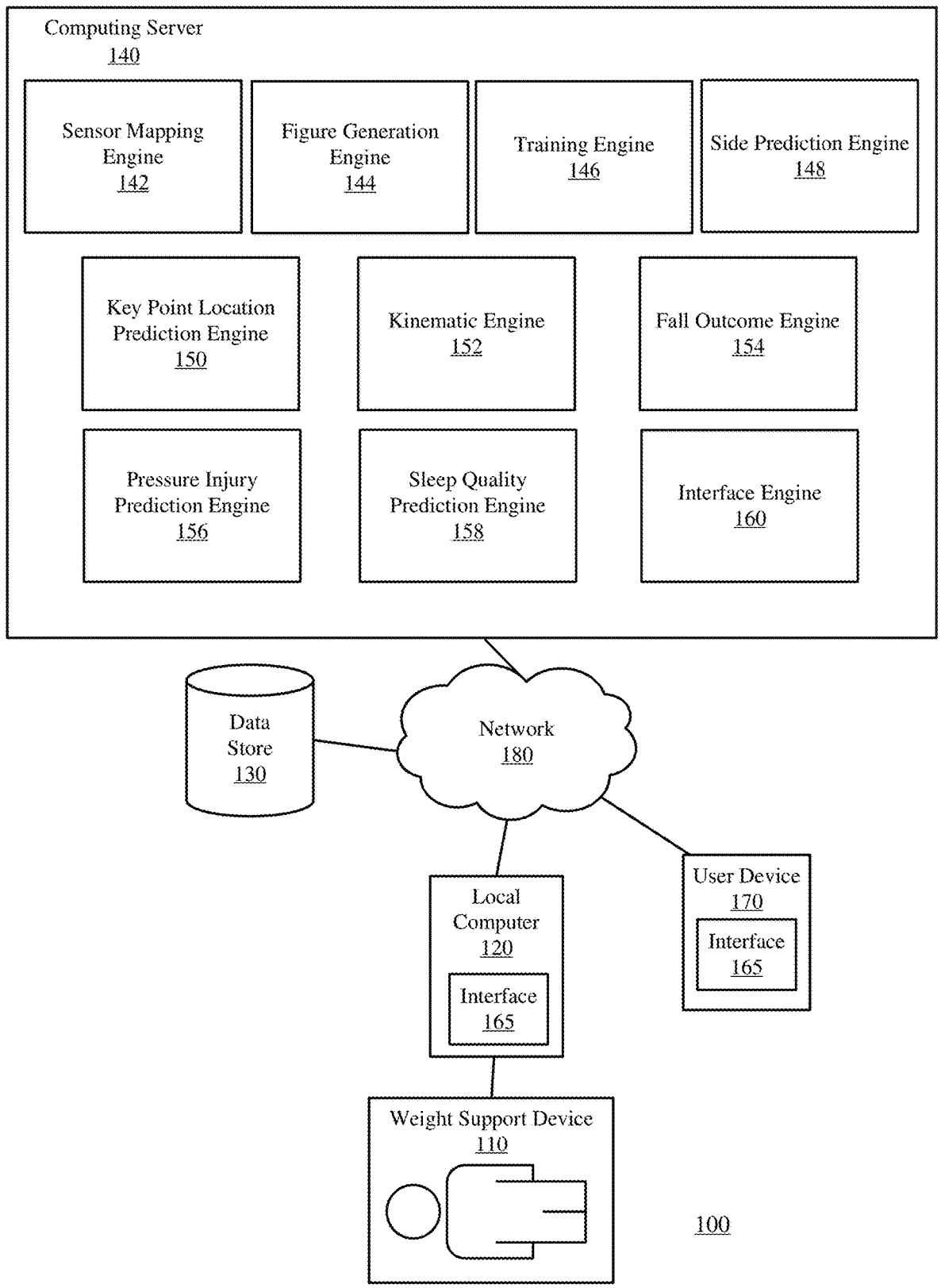
FIG. 1 is a block diagram illustrating an example system environment, in accordance with some embodiments.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Configuration Overview

Embodiments described herein relate to a weight support device, which may be referred to as an intelligent sheet (or surface), for wireless monitoring of pressure, surface moisture, surface temperature, vital signs, and a variety of other useful clinical information. The intelligent surface may take the form of a portable and flexible mat that can provide the clinical information without any direct wiring connected to a user supported by the weight support device. The user may include a patient in a hospital, a patient in an elderly care setting, a user at home, etc. In some embodiments, the intelligent surface simply serves as a pad, a mattress, or a support layer for the user to sleep, sit, or otherwise rest upon. The weight support device may include a fitted sheet, mattress, overlay, or topper with one or more embedded capacitive sensor layers, which may be combined with other sensing technologies including piezoelectric sensors, accelerometers, thermistors, or others.

In accordance with some embodiments, a computer receives raw pressure data (e.g., generated from an embedded capacitive sensor layer in a weight support device supporting an individual) collected over a measurement period. The pressure data indicates levels of pressure at various locations of the weight support device caused by the weight of the user pressing against the weight support device. The human body can be represented by a plurality of segments connected by a plurality of joints, and the computer determines, at a given time during the measurement period, key point locations (e.g., two-dimensional coordinates of the plurality of joints) and a side of the user that is in contact with the weight support device (e.g., the side that the user is sleeping on) based on the pressure data. After determining the key point locations and the side, a virtual figure representing the user is generated to represent a pose of the user at the given time. The virtual figure representing the user may be presented (e.g., to the user, to the user's caretaker, to the user's doctor) as a video including a plurality of frames, where each frame illustrates a pose of the user at a different time during the measurement period. The virtual figure is adjusted in each frame to show how the user moved throughout the night.

In accordance with some other embodiments, a computer receives raw pressure data (e.g., generated from an embedded capacitive sensor layer in a weight support device supporting an individual) collected over a measurement period. The pressure data indicates levels of pressure at various locations of the weight support device caused by the weight of the user pressing against the weight support device. The pressure data is fed into a machine learning model or alternative processing mechanism to directly generate a virtual figure representing the user to represent a pose of the user at the given time. The virtual figure representing the user may be presented (e.g., to the user, to the user's caretaker, to the user's doctor) as a video including a plurality of frames, where each frame illustrates a pose of the user at a different time during the measurement period. The virtual figure is adjusted in each frame to show how the user moved throughout the night.

In accordance with some embodiments, several signal processing modules and machine learning models are used to detect pressure injury outcomes, fall outcomes, body/joint/limb position, body movement, activity level, seizures, surface/bed occupancy, and sleep quality. Biometrics can be derived from the signals of the intelligent surface may include but are not limited to body position, key point locations, and movement monitoring. The intelligent surface may be associated with an artificial intelligence system, which may use multiple types of machine learning models to identify the individual's pressure injury outcome (e.g., a risk of developing a pressure injury, an area of the individual's body at risk of developing the pressure injury, and an amount of time that indicates when an adjustment of a positioning of the user is needed to avoid pressure injury), the individual's fall outcome (e.g., a risk of falling off the weight support device (the intelligent surface) and an indication a fall took place), and/or the individual's sleep quality (e.g., a score representing how well the user slept during the night).

Example System Environments

FIG. 1 is a block diagram illustrating an example system environment 100, in accordance with some embodiments. The system environment 100 includes a weight support device 110, a local computer 120, a data store 130, a computing server 140, and a user device 170. In other embodiments, the system environment 100 may include fewer, different, or additional components. While some of the components in the system environment 100 may be described in singular form, the system environment 100 may include one or more of each of the components (e.g., multiple weight support devices 110, multiple user devices 170 for accessing the computing server 140).

The weight support device 110 may include layers that support the weight or part of the weight of a user (e.g., a patient) and include sensors that monitor various data associated with the person. Examples of the weight support device 110 include a bedding system (e.g., a mattress), a seating system (e.g., a wheelchair, a dining chair, an office chair, a car seat), a sheet, a cushion, a pillow, a pad, etc. The weight support device 110 may also be referred to as an intelligent surface. While in this disclosure the weight support device 110 is often described as a bedding system, various features and components of the bedding system may also be applied to other types of the weight support device 110 without explicitly referring to those types of the weight support device 110. The weight support device 110 may come in various sizes and different forms. For example, a bedding system may be an intelligent mattress that may include various comfort layers such as foam. In another example, a bedding system may be a pad that is intended to complement a conventional mattress (e.g., being laid on top of the mattress). A bedding system may also be used in a special setting such as in the hospital or elderly care facility. The weight support device 110 may also be a seating system that can be used as an intelligent office seat that monitors the posture of a person, a car seat (or a cushion for a car seat), or a wheelchair seat.

The weight support device 110 may generate sensor signals and be in communication with a computer. The weight support device 110 may take the form of a portable flexible mat that can provide biometric information without any direct wiring connected to the person. The weight support device 110 may measure the pressure exerted by the user using a sensor grid to generate a matrix of pressure readings. The matrix of pressure readings may be provided to a computer with an artificial intelligence system which uses one or more types of machine learning networks (a convolutional neural network (CNN), a long short term memory (LSTM) network, etc.) to predict which side the user is sleeping on, key point locations of the person, predict fall outcome (e.g., a risk of the user falling off the weight support device 110), predict pressure injury outcome (e.g., a risk of the user developing a pressure injury), generate a virtual figure, and/or determine sleep quality. The matrix of pressure readings may be supplemented with other sensor readings to deduce other information about the user that may include, but is not limited to, respiration rate and heart rate.

In some embodiments, the weight support device 110 may be connected to a local computer 120 that is located, for example, in the same place as the weight support device 110 (e.g., in a patient's hospital room). In some embodiments, the weight support device 110 may be equipped with processing power such as having built-in CPUs or the local computer 120 being part of the weight support device 110. In other embodiments, the local computer 120 may be a separate computer that connects to the weight support device 110 to collect data from the weight support device 110. The local computer 120 may upload the data via the network 180 to the computing server 140 for further processing. In some embodiments, the local computer 120 may also have software installed to analyze the data from the weight support device 110. For example, in a hospital setting, the local computer 120 may be a bedside monitor that provides analyses of various data in real-time and display the data associated the patient. In other embodiments, the local computer 120 simply collect data or perform certain data processing (such as compression, conversion of formats) for the computing server 140 to further analyze the data. The role of the local computer 120 may vary in different implementations and settings. In some embodiments, local computer 120 may not be present. For example, the weight support device 110 may be equipped with a wireless capability that can directly transmit its data to the computing server 140 for processing. Details on the weight support device 110 are discussed in U.S. patent application Ser. No. 17/339,401, filed on Jun. 4, 2021, entitled "Intelligent Patient monitoring System," which is incorporated by reference herein for all purposes.

In some embodiments, a weight support device 110 (or a computer that processes the raw data of the weight support device 110) may transmit data in a secure network environment to a caretaker (e.g., a healthcare professional) via a management dashboard (e.g., at a nursing station, front management desk in a retirement home, etc.) of a user device 170 to highlight the state and status of the user being monitored. The user device 170 may also provide an alert system alerting the caretaker that a user is at risk of developing a pressure injury and/or at risk of falling off the weight support device 110, that an adjustment of a positioning of the patient is needed, when the adjustment is needed, etc. The user device 170 may be communicatively coupled to more than one weight support device 110 and provide the status of multiple users to the caretaker. The user device 170 may prioritize the users and provide their status accordingly based on each user's risk of developing a pressure injury and/or risk of falling, when each user needs their positioning adjusted, and/or how long an area or areas of each user has been experiencing high-pressure.

While sleep monitoring using a weight support device 110 is used as the primary example to describe the various systems and processes in this disclosure, other types of posture monitoring and weight support devices may also be used in various embodiments. For example, in some embodiments, the weight support device may take the form of a chair (e.g., office chair, wheelchair) with pressure sensors at the seat, the lumbar support, potentially the neck support. The pressure sensors may be used to track key point locations of the user while the user is sitting on the chair. A virtual figure may be generated to simulate the sitting posture of the user based on the key point locations.

The computing server 140 may be a remote server that is used to analyze pressure data collected from the weight support device 110. The computing server 140 may take the form of a combination of hardware and software, such as a sensor mapping engine module 142, a figure generation engine module 144, a training engine module 146, a side prediction engine module 148, a key point location prediction engine module 150, a kinematic engine module 152, a fall outcome engine module, a pressure injury prediction engine module 156, a sleep quality prediction engine module 158, and an interface engine module 160. The computing server 140 may include some or all example components of a computing machine described with FIG. 9. In other embodiments, the computing server 140 may take different forms and include fewer, different, or additional engine modules. In one embodiment, the computing server 140 may be a server computer that executes code instructions to cause one or more processors to perform various processes described herein. In another case, the computing server 140 may be a pool of computing devices that may be located at the same geographical location (e.g., in a server room) or be distributed geographically (e.g., cloud computing, distributed computing, or in a virtual server network). The computing server 140 may also include one or more virtualization instances such as a container, a virtual machine, a virtual private server, a virtual kernel, or another suitable virtualization instance.

The sensor mapping engine module 142 may organize the data measured by the array of pressure sensing elements in the weight support device 110 into an array of measurements representative of the sensor array. An example of an array of sensor measurements is illustrated in FIG. 2A.

Figure 2A:
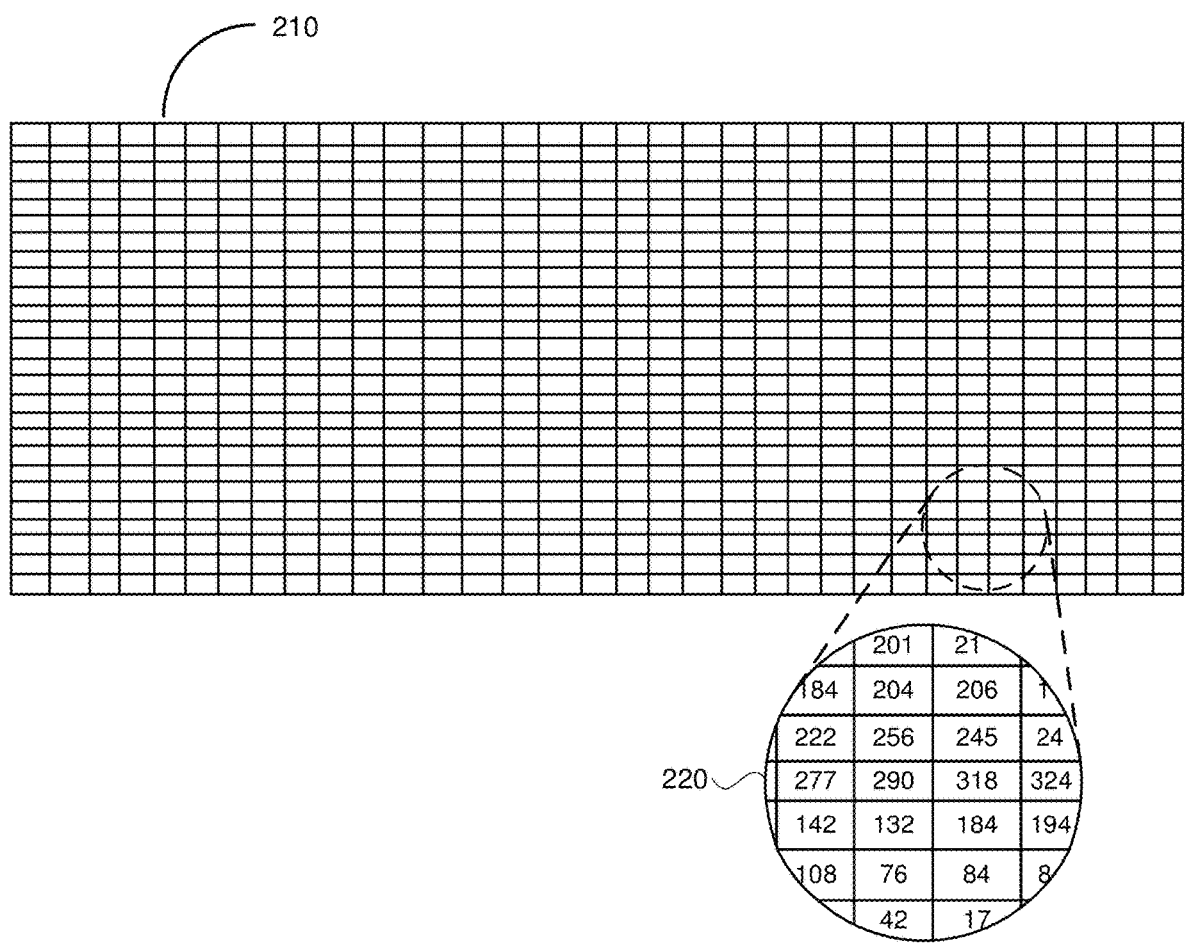
FIG. 2A is a conceptual diagram of a matrix of pressure sensor readings generated by a sensor grid, in accordance with some embodiments.

FIG. 2A is a conceptual diagram of a matrix 210 of sensor readings generated by a sensor grid, in accordance with some embodiments. The sensor grid of the weight support device 110 includes a plurality of sensors, where each sensor can generate a pressure reading. The signals from the sensor grid may generate the matrix 210 of sensor readings. An inset 220, which shows an enlarged area of the matrix 210 illustrates that each grid position that corresponds to a sensor provides a sensor reading value at the grid location. A computer (e.g., the computing server 140) may process the data from the sensor grid and generate results related to the user that is on the weight support device 110. When the user is on the weight support device 110, the weight of the user compresses the sensor grid, causing the sensor grid to output the matrix 210 of sensor readings corresponding to the compression.

Referring back to FIG. 1, the sensor mapping engine module 142 may calculate an average peak pressure over the entire sensing area of the weight support device 110. In one approach, the sensor mapping engine module 142 may calculate an average peak pressure by isolating a group of sensors with the highest measured pressures (the peak pressures), then averaging those pressure values to obtain the result. For example, using a bed sensor with 1664 sensors in the sensor area, the 16 sensors with the highest pressure measurements could be averaged to determine the average peak pressure. The number of sensors averaged could be 25% to 0.5%, or preferably 1%, of the total number of sensors in the array. The number of sensors averaged could also be 25% to 0.5%, or preferably 1%, of the total number of sensors in the array that are above a pressure threshold, for example, 10 mmHg. The sensor mapping engine module 142 may reject certain peak pressures in order to reduce the impact of creases in the sensor grid, objects in the customer's pockets, or hard edges in the customer's clothing. For example, the three highest pressure measurements can be excluded from the average peak pressure calculation.

The sensor mapping engine module 142 may calculate a load calculation (e.g., another pressure-related parameter) based on the sensor data. For example, a load calculation could be used to estimate a person's weight. The sensor mapping engine module 142 may estimate the person's height by adding the number of sensors associated with a pressure reading greater than a minimum pressure from the person's head to their toes when they are lying on their back. Similarly, the sensor mapping engine module 142 may estimate a shape of the person's body (e.g., length of arms and legs) by adding the number of sensors associated with a pressure reading greater than a minimum pressure for various segments of the person's body.

The sensor mapping engine module 142 may calculate a mass distribution for the user. For example, the sensor mapping engine module 142 creates a peak pressure curve along a length of a person lying on the weight support device. The mass distribution may be calculated from applied pressure over a given unit area. For example, the sensor mapping engine module 142 may calculate a mass for each individual sensor in the sensing array by multiplying the measured pressure by the area of the sensor. Mass can also be calculated for larger areas by averaging pressure measurements over a group of sensors, for example, 2×2 or 4×4 sensor. The figure generation engine module 144 can create a body mass curve along the length of a user lying on their back or side. The peak pressure curve and/or the body mass curve can also be used for matching a person to their physical profile. The sensor mapping engine module 142 may calculate a center of mass for the user based on the mass calculations for all areas within the contact area and a position of each area in the contact area.

The average peak pressure, load calculation, the mass distribution, and other information determined by the sensor mapping engine module 142 from the pressure data may be used by any of the other engine modules in the computing server 140.

The figure generation engine module 144 generates a virtual figure representative of the user, and may include a machine learning model or alternative processing mechanism in some embodiments. A virtual figure is a graphical representation of the user. The virtual figure may be rendered (e.g., on the local computer 120, the user device 170) to illustrate the movements of the user determined by the sensor data collected by the weight support device 110. The virtual figure may be a two-dimensional representation (e.g., stick figure, cartoon figure) or a three-dimensional representation (e.g., 3D avatar). In some embodiments, the virtual figure may be scaled to be similar to a physical profile of the user. A physical profile includes physical attributes such as measurements of certain body features, for example, height, weight, shoulder-width, hip-width or waist-width; or ratios of these measurements, for example, shoulder to hip ratio, shoulder to waist ratio, or waist to hip ratio; body type, for example, endomorph, ectomorph, endomorph; or Body Mass Index (BMI). The figure generation engine module 144 may determine the physical profile based on sensors readings analyzed by the sensor mapping engine module 142 and/or user input.

In some embodiments, the virtual figure includes a head representation, a torso representation, and a limb representation for each limb (e.g., left arm, right arm, left leg, right leg) to represent various body parts. At least one limb representation may include a plurality of segments connected to each other by joints. For example, the limb representation for an arm includes a hand representation, a forearm representation, and an upper arm representation. The hand representation is attached to the forearm representation by a wrist joint, the forearm representation is attached to the upper arm representation by an elbow joint, and the upper arm representation is attached to the torso representation by a shoulder joint. As another example, the limb representation for a leg includes a foot representation, a shin representation, and a thigh representation. The foot representation is attached to the shin representation by an ankle joint, the shin representation is attached to the thigh representation by a knee joint, and the thigh representation is attached to the torso representation by a hip joint. In one embodiment, the virtual figure includes 14 joints: left ankle, right ankle, left knee, right knee, left hip, right hip, sacrum, left wrist, right wrist, left elbow, right elbow, left shoulder, right shoulder, and effector head. A key point location may correspond to coordinates (2D or 3D) of a readily traceable body part with respect to the weight support device 110. For example, a key point location can be a location of a joint, a center of mass of a body part, or another suitable traceable body location, such as the tip of the head, the tip of a toe, two-third of an arm, etc.

The figure generation engine module 144 may adjust the virtual figure by changing the relative positions of the various segments in the virtual figure to illustrate the movements of the user during a measurement period. For example, the measurement period may be a duration during which the weight support device 110 collects pressure data while the user sleeps on the weight support device 110. The figure generation engine module 144 may adjust the virtual figure to represent a pose of the user at various timestamps based on the outputs of the kinematic engine module 152 that predicts relative positions of the head representation, the torso representation, and the limb representations based on key point location predictions (e.g., determined by the key point location prediction engine module 150) and side predictions (e.g., determined by the side prediction engine module 148).

Figure 2B:
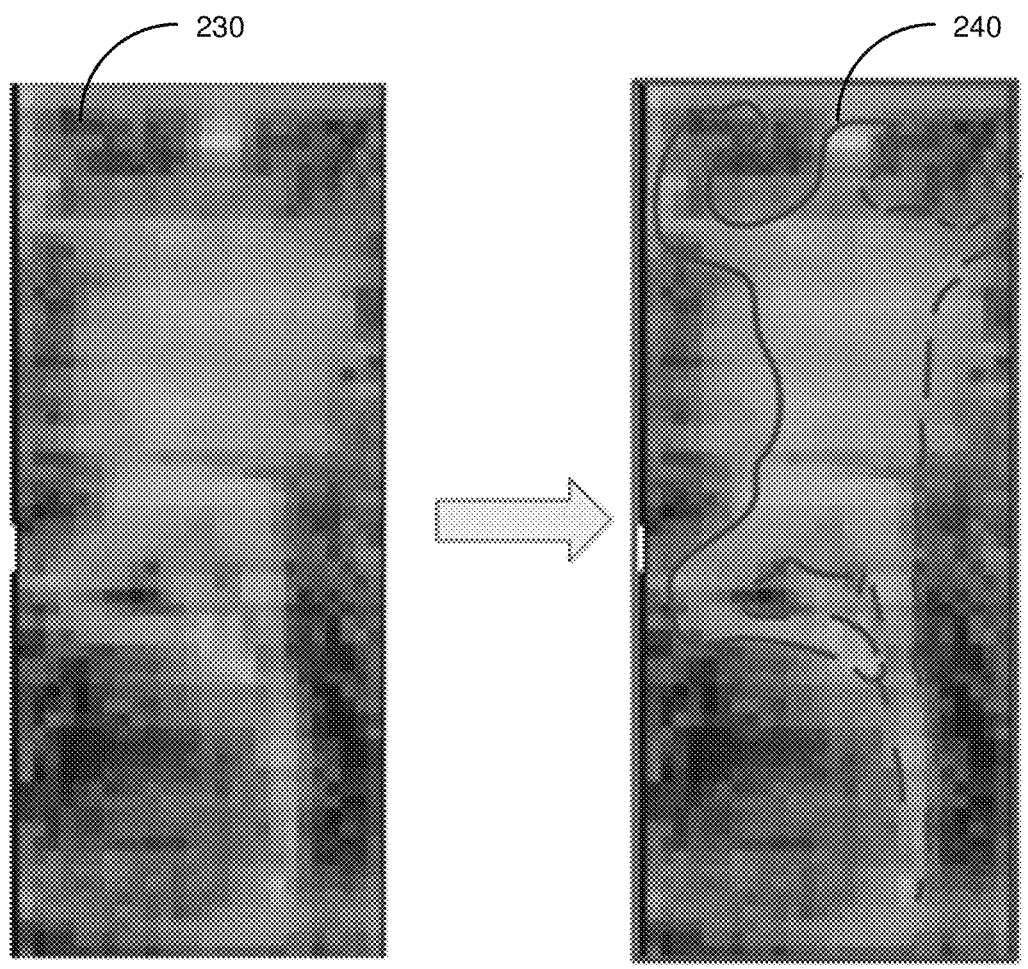
FIG. 2B is a conceptual diagram of a matrix of sensor readings being used to generate a virtual figure, in accordance with some embodiments.

In some embodiments, the figure generation engine module 144 uses sensor data to automatically match the user on the weight support device 110 to a virtual figure previously stored (e.g., in the data store 130). The figure generation engine module 144 may generate a virtual figure for a particular user during a set up phase when the user first uses the weight support device 110 and store the virtual figure to be used again. When the user subsequently lies down on the weight support device 110, the figure generation engine module 144 may determine physical attributes (e.g., height, weight) based on the sensor data and compare the physical attributes to virtual figures in the data store. In another embodiment, the figure generation engine module 144 receives a user identification (e.g., from the user device 170 or the local computer 120) to determine which virtual figure to use. In another embodiment, the figure generation engine module 144 receives pressure data and generates a virtual figure directly. As illustrated in FIG. 2B, the figure generation engine module 144 may generates a visual representation 230 of the sensor data and detect edges 240 of the user's body to determine the shape of the user's body. Using the outline of the user's body determined from the sensor data may improve accuracy of the virtual figure. For example, the outline can be used to determine length and width of various parts of the user's body that can be used to scale the virtual figure.

The training engine module 146 trains various machine learning models of the computing server 140 applied by the side prediction engine module 148, the key point location prediction engine module 150, the fall outcome engine module 154, the pressure injury prediction engine module 156, and the sleep quality prediction engine module 158. The training techniques for a machine learning model may be supervised, semi-supervised, or unsupervised. In supervised learning, the machine learning models may be iteratively trained with a set of training samples that are labeled.

In some embodiments, a machine learning model used by the side prediction engine module 148 receives pressure data collected by the weight support device 110 as input and outputs a side label that identifies which side of the user was in contact with the weight support device 110 at the time the pressure data was collected. In one embodiment, the side label may be one of the following: prone, supine, left side, right side. Each training sample for training the machine learning model may include historical pressure data collected by the weight support device 110 while a historical user is lying on the weight support device 110 and a corresponding side label identifying which side of the historical user's body was in contact with the weight support device 110 at the time the historical pressure data was collected. In one embodiment, to determine which side label is associated with the training sample, an image of the historical user lying on the weight support device 110 is presented to an annotator that reviews the image and provides the side label. In another embodiment, the image of the historical user may be provided to an image recognition mode (which is another machine learning model) that is trained to determine which side of the user is in contact with the weight support device 110. In yet another embodiment, an image of the historical user may not be used, and the historical user or an observer may provide the side label in association with the pressure data. Details on applying the trained machine learning model is described below with respect to FIG. 3.

In some embodiments, a machine learning model used by the key point location prediction engine module 150 receives pressure data collected by the weight support device 110 as input and outputs key point locations. The machine learning model may be trained with training samples, where each training sample includes historical pressure data collected by the weight support device 110 at a given time and labels of key point locations corresponding to a pose that the historical user was in at the time. The labels of key point locations may be provided by annotators. In one embodiment, sensor data from the weight support device 110 may be converted to various colors or greyscales to illustrate pressure distribution on the weight support device 110 for a historical user and presented to an annotator. For example, the pressure heatmap may be a greyscale heatmap in which higher pressure values are associated with darker colors. Because the area of the weight support device 110 without a user should detect significantly less pressure than the area on which the user is currently positioned on, the area without the user may be represented in white. The pressure heat map may show the shape of the user's body, and the annotator may interact with the pressure heat map to indicate where the different joints are located with respect to the pressure heat map (e.g., click on a first point on the heatmap and label the point as "left knee, click on a second point on the heatmap and label the point as "effector head"). In some embodiments, the heatmap may also be in a color scheme. For example, low-pressure areas will be shown using cooler colors and high-pressure areas will be shown using warmer colors. In some embodiments, the pressure heatmap may be presented to the annotator with an image of the user lying on the weight support device 110 to help the annotator determine which part of the heatmap corresponds to the joints. For example, when the user is lying on their left side, it may be difficult to determine where the right elbow joint or right shoulder joint are from just the pressure heatmap, so the image of the user may assist the annotator for labelling. In other embodiments, the annotator may be presented with just the image (without the heatmap), and the annotator may label the joints with respect to the image. The image may be aligned with the pressure sensors in the weight support device 110, and the labels on the image may be mapped onto the pressure data. Details on applying the trained machine learning model is described below with respect to FIG. 3.

In some embodiments, a machine learning model used by the fall outcome engine module 154 is receives pressure data collected by the weight support device 110 as input and outputs a prediction of fall outcome. In some embodiments, the models may monitor the pressure data in real-time for any anomalies and based on a detected anomaly determine the fall outcome. In some embodiments, the models may be trained to detect a fall occurred (i.e., that the person experienced a fall) as opposed to the person getting off-of or out-of the weight support device 110 on purpose. In these embodiments, the fall outcome may include a risk of the person falling off of the weight support device 110 and/or an indication that a fall occurred.

In some embodiments, a machine learning model used by the pressure injury prediction engine module 156 is trained to classify body parts at risk of developing a pressure injury. The training samples may be different heatmaps of pressure data labeled with body parts that did and did not develop pressure injuries. In another example, in a machine learning model trained to detect a likely fall, the training samples may be different heatmaps of pressure data labeled with either a yes or no (e.g., a 1 or 0) indicating the person did experience a fall or did not experience a fall. Thus, the labels for each training sample may be binary or multi-class.

In some embodiments, another machine learning model used by the pressure injury prediction engine module 156 is trained to determine when a person should have their position adjusted to avoid a pressure injury. The training samples may be historical data of individuals who developed a pressure injury (e.g., each individual's pressure data and health record). For training a binary machine learning model (e.g., a model that identifies whether a person develops pressure injury, whether a particular body part of a person develops a pressure injury, etc.), training samples may include a positive training set (with training samples that have the label of having a pressure injury) and a negative training set (with training samples that have the label of not having a pressure injury). In some cases, an unsupervised learning technique may be used. The samples used in training are not labeled. Various unsupervised learning techniques such as clustering may be used. In some cases, the training may be semi-supervised with the training set having a mix of labeled samples and unlabeled samples.

Details on fall prediction and pressure injury prediction are discussed in U.S. patent application Ser. No. 17/339,401, filed on Jun. 4, 2021, entitled "Intelligent Patient monitoring System," which is incorporated by reference herein for all purposes.

In some embodiments, a machine learning model used by a sleep quality prediction engine module 158 is trained to determine a quality of a user's sleep based on pressure data collected over a measurement period (e.g., a score representing the sleep quality). The training samples may be historical pressure data of historical users collected over various measurement period and a score representing the sleep quality. The score may be determined based on input from the historical users. For example, after a measurement period, the historical users may be asked to answer a set of questions regarding their conditions after waking up from their sleep and a score may be generated based on the answers or the historical users may provide the scores to rate their sleep. In some embodiments, the machine learning model for determining the sleep quality may be used in combination with the machine learning models for the side prediction engine module 148, the key point location prediction engine module 150, the fall outcome engine module 154, and/or the pressure injury prediction engine module 156. For example, if the fall outcome engine module 154 determines that the user fell from the weight support device 110 or that there is a high risk of pressure injury, the machine learning model may determine that the sleep quality was poor.

In some embodiments, another machine learning model is trained to generate a virtual figure based on pressure sensor data.

A machine learning model may be associated with an objective function, which generates a metric value that describes the objective goal of the training process. For example, the training may intend to reduce the error rate of the model in generating predictions. In such a case, the objective function may monitor the error rate of the machine learning model. In object recognition (e.g., object detection and classification), the objective function of the machine learning algorithm may be the training error rate in classifying objects in a training set. Such an objective function may be called a loss function. Other forms of objective functions may also be used, particularly for unsupervised learning models whose error rates are not easily determined due to the lack of labels. In pressure injury outcome detection, the objective function may correspond to the difference between the model's prediction of a person developing a pressure injury and the manually identified development of a pressure injury in the training sets. In fall outcome detection, the objective function may correspond to the difference between the model's prediction that a person may experience a fall and the manually identified fall(s) experienced by the person in the training set. In various embodiments, the error rate may be measured as cross-entropy loss, L1 loss (e.g., the sum of absolute differences between the predicted values and the actual value), L2 loss (e.g., the sum of squared distances).

To determine the user's movement during a measurement period, the kinematic engine module 152 receives side predictions from the side prediction engine module 148 and key point location predictions from the key point location prediction engine module 150 and predicts how segments of body parts moved relative to each other. As described above, the human body can be represented as a plurality of segments that are connected by joints. For the virtual figure including a head representation, a torso representation, and limb representations, the torso representation is the base from which the head representation and the limb representations extend. For the limb representations, the segments and joints in the virtual figure have a hierarchical structure, where a root joint (e.g., shoulder joint for arm, hip joint for leg) connects the rest of the segments to the torso representation. Each joint is associated with a degree of freedom that constrains the motion of the segments that are connected by the joint. The kinematic engine module 152 models the range of motion of the human body using a set of kinematic equations given the degrees of freedom of the various joints. The kinematic engine module 152 determines how the different representations of the body parts in the virtual figure move from timestamp to timestamp during the measurement period and provides details on the movement to the figure generation engine module 144. Based on the movement details, the figure generation engine module 144 may adjust the virtual figure to mirror the movements of the user.

Figure 5A:
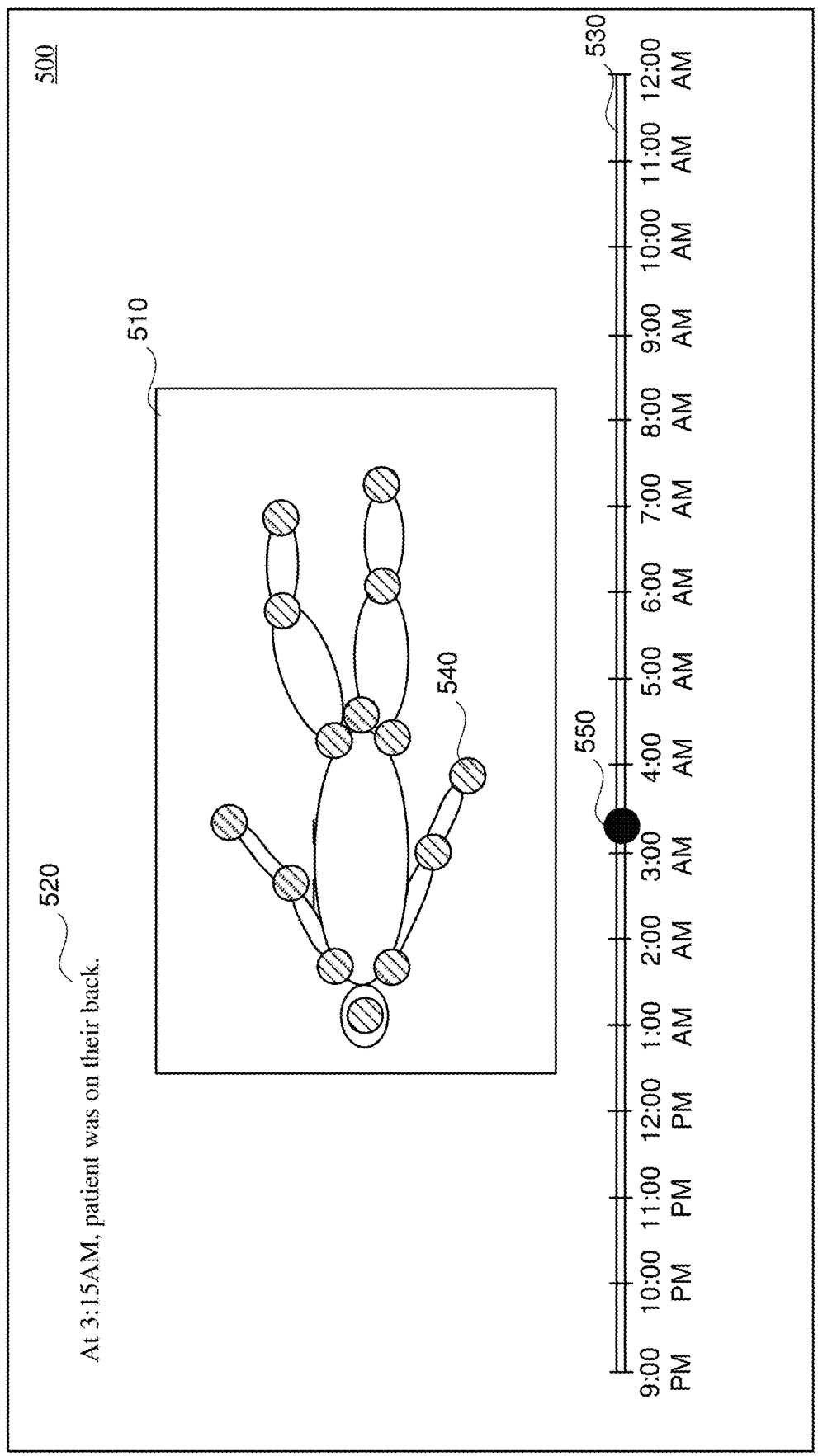
FIGS. 5A and 5B illustrate an example graphical user interface in the system illustrating a virtual figure representing a user at two different time stamps, in accordance with some embodiments.
Figure 5B:
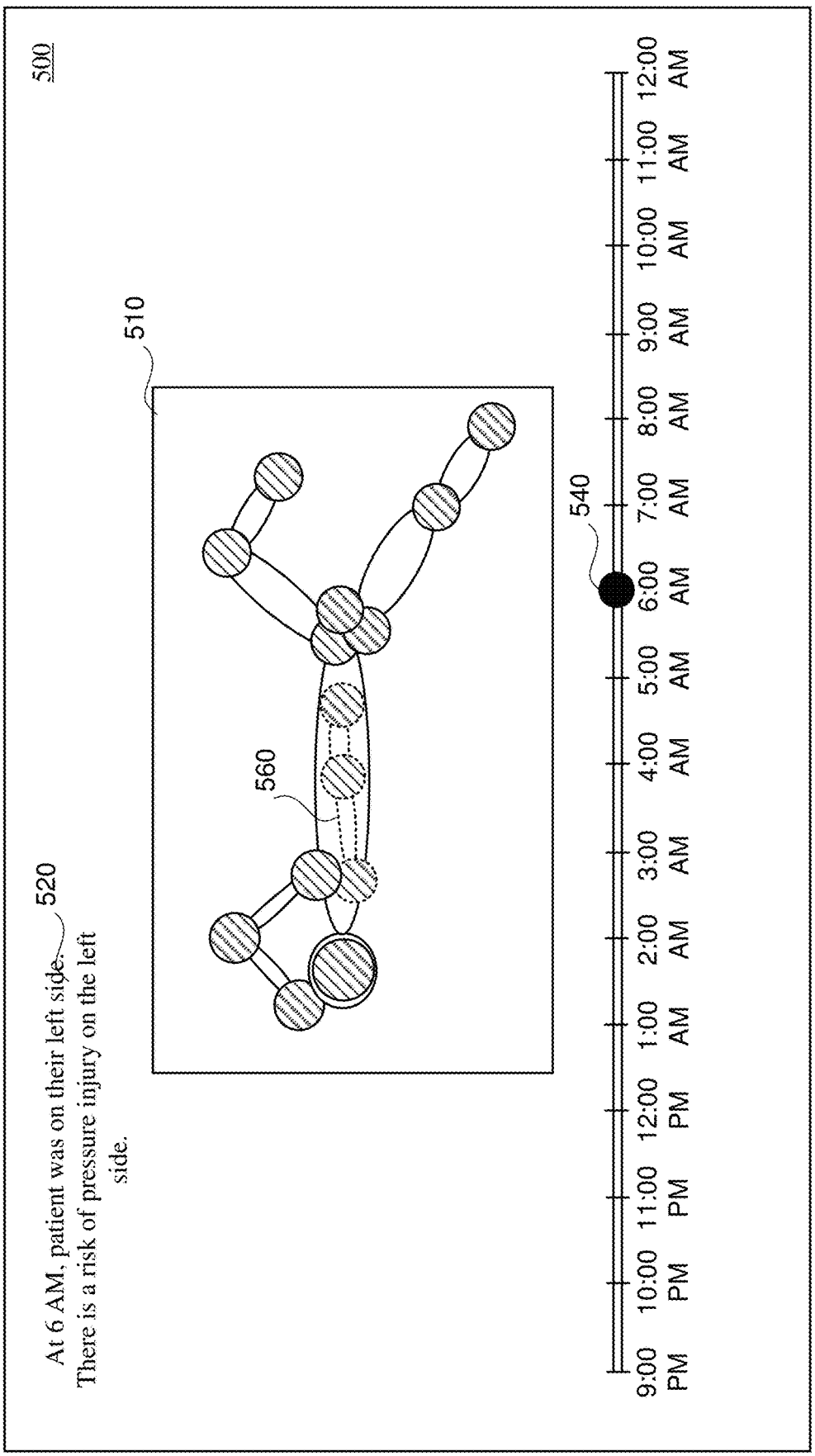

The interface engine module 160 generates the interface 165 to present the virtual figure generated by the figure generation engine module 144 and analysis performed by the computing server 140. The interface 165 may be a suitable interface for the local computer 120 and/or the user device 170 to interact with the computing server 140. The interface 165 may include various visualizations and graphical elements to display notifications and/or information to users and may also include input fields to accept inputs from users. An example interface 165 is illustrated in FIGS. 5A-5B. A user may communicate to the application and the computing server 140 through the interface 165. The interface 165 may take different forms. In one embodiment, the interface 165 may be a web browser such as CHROME, FIREFOX, SAFARI, INTERNET EXPLORER, EDGE, etc. and the application may be a web application that is run by the web browser. In another application, the interface 165 is part of the application. For example, the interface 165 may be the front-end component of a mobile application or a desktop application. The interface 165 also may be referred to as a graphical user interface (GUI) which includes graphical elements to display a digital heatmap, other pressure injury-related information, or other fall-related information. In another embodiment, the interface 165 may not include graphical elements but may communicate with the computing server 140 via other suitable ways such as application program interfaces (APIs).

The data store 130 includes one or more storage units such as memory that takes the form of non-transitory and non-volatile computer storage medium to store various data that may be uploaded by the local computer 120, by the weight support device 110, or by other components of the system environment 100. The computer-readable storage medium is a medium that does not include a transitory medium such as a propagating signal or a carrier wave.

In some embodiments, the data store 130 stores health records of person(s) supported by the weight support device 110. The health records may have been input into the data store 130 by the local computer 120, the user device 170, etc. at any time. Each health record corresponds to a particular user and includes information about the person, such as an age, mobility information, nutrition information, pre-existing skin conditions, incontinent issues, medical history, current medications, results of blanch test, the physical profile, etc. The health record may also include information about one or more areas of the user (e.g., a wound site, a surgical site, etc.) that are to avoid pressure. The data store 130 may store sensor data (e.g., pressure data) captured by the weight support device 110 and also analysis results generated by the computing server 140, such as determined position data, pressure injury outcome(s), and/or fall outcome(s). The sensor data and analysis results corresponding to a particular user may be associated with a health record of that user and stored within the health record. In some embodiments, the data store 130 aggregates sensor data received from multiple weight support devices 110 by which the user has been supported. For example, in a hospital setting, a patient may be admitted to the hospital by a wheelchair, be treated on a first bedding system (e.g., a stretcher) in an emergency care and be transferred to a second bedding system (e.g., a hospital bed) in a patient room. The data store 130 may receive data from the wheelchair, the first bedding system, and the second bedding system for the computing server 140 to continuously monitor the pressure readings related to the patient.

The data store 130 may store historical patient data. The historical patient data includes health record data, sensors data, and analysis results for patients that have historically been supported by the weight support device 110. The historical patient data may be utilized by one or more machine learning models to train the models to determine pressure injury outcomes and/or fall outcomes for current or future patients.

The data store 130 may take various forms. In one embodiment, the data store 130 communicates with other components by the network 180. This type of data store 130 may be referred to as a cloud storage server. Example cloud storage service providers may include AWS, AZURE STORAGE, GOOGLE CLOUD STORAGE, etc. In another embodiment, instead of a cloud storage server, the data store 130 is a storage device that is controlled and connected to the computing server 140. For example, the data store 130 may take the form of memory (e.g., hard drives, flash memories, discs, ROMs, etc.) used by the computing server 140 such as storage devices in a storage server room that is operated by the computing server 140.

The user device 170 may be a portable electronic device for transmitting data. The user device 170 may be possessed by the user using (e.g., supported by) the weight support device 110. The user device 170 may be possessed by a different user in the system environment 100. For example, the user device 170 may be used by a healthcare professional, caregiver, etc. Examples of user devices 170 include personal computers (PCs), desktop computers, laptop computers, tablet computers, smartphones, wearable electronic devices such as smartwatches, or any other suitable electronic devices. The user device 170 may include an application such as a software application provided by the computing server 140. The application may provide various results and analyses of the sensor data collected by the weight support device 110 and may also allow the user and/or the user to adjust various settings associated with weight support device 110. An application may be of different types. In one case, an application may be a web application that runs on JavaScript, etc. In the case of a web application, the application cooperates with a web browser to render a front-end interface 165. In another case, an application may be a mobile application. For example, the mobile application may run on Swift for iOS and other APPLE operating systems or on JAVA or another suitable language for ANDROID systems. In yet another case, an application may be a software program that operates on a desktop computer that runs on an operating system such as LINUX, MICROSOFT WINDOWS, MAC OS, or CHROME OS.

The various functionalities of the computing server 140 may also be performed by the local computer 120 or the user device 170, depending on the implementation and configuration. For example, one or more software algorithms that perform various processes associated with engine modules 142, 144, 146, 148, 150, 152, 154, 156, 158, and 160 in the computing server 140 may also reside in the local computer 120 or a mobile application of the user device 170 so that the local computer 120 or the user device 170 may directly analyze the sensor data generated by the weight support device 110. Results generated may be displayed at the user device 170, at the local computer 120, or at both devices. The computing server 140 may manage a mobile application that can cause the local computer 120 or the user device 170 to generate a user interface 165 that displays various results, predictions, determinations, notifications, visual representations, and graphical illustrations of sensor data generated by the weight support device 110. In some embodiments, the weight support device 110 may also include computing components and software for analyzing the data directly and display the results. In some embodiments, the computing server 140 may be absent and the generation of the user's figure and other determinations may be performed locally by the local computer 120 or the user device 170. For example, the user device 170 may include a mobile application that performs various computations described in the engine module 142 through 160. In some embodiments, some of the computations may be performed by the computing server 140 while other computations are performed by the local computer 120 or the user device 170. In various embodiments, one or more devices (e.g., the local computer 120, the computing server 140, and/or the user device 170, individually or in combination) that perform various computer-implemented processes described in this disclosure may be referred to as a computing device or simply as a computer.

The network 180 provide connections to the components of the system environment 100 through one or more sub-networks, which may include any combination of the local area and/or wide area networks, using both wired and/or wireless communication systems. In one embodiment, the network 180 use standard communications technologies and/or protocols. For example, a network 180 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 180 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 180 may be represented using any suitable format, such as hypertext markup language (HTML), extensible markup language (XML), JavaScript object notation (JSON), structured query language (SQL). In some embodiments, all or some of the communication links of a network 180 may be encrypted using any suitable technique or techniques such as secure sockets layer (SSL), transport layer security (TLS), virtual private networks (VPNs), Internet Protocol security (IPsec), etc. The network 180 also include links and packet switching networks such as the Internet.

Example Virtual Figure Generation Process

Figure 3:
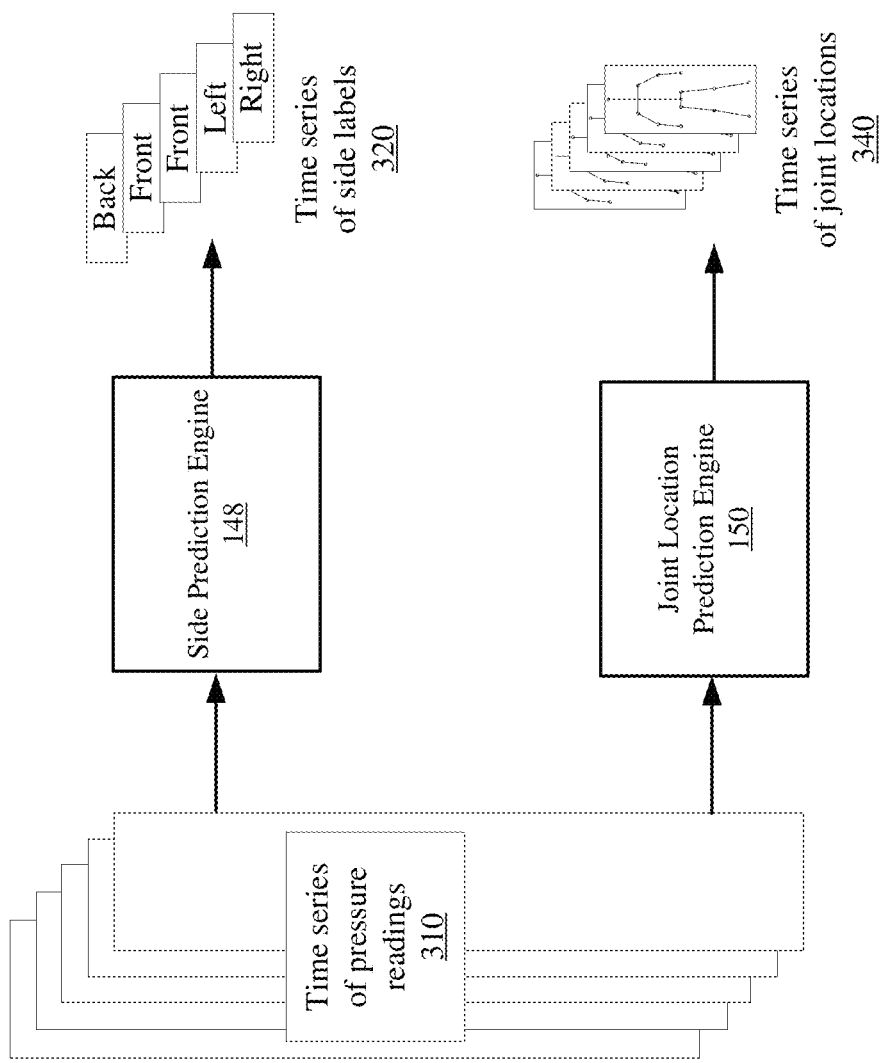
FIG. 3 is a conceptual diagram illustrating an example pipeline in the system consisting of a side prediction engine module and a joint location prediction engine module for making side predictions and key point location predictions, in accordance with some embodiments.

FIG. 3 is a conceptual diagram illustrating an example algorithmic pipeline for making side predictions and key point location predictions, in accordance with some embodiments. Each of the side prediction engine module 148 and the key point location prediction engine module 150 may receive a time series of pressure readings 310 (e.g., a time series of pressure data) and perform various analyses on the pressure readings 310. The analyses are related to predicting a time series of side labels 320 and predicting a time series of key point locations 340 at several instances in time during a measurement period, respectively. In some embodiments, the time series of pressure readings 310 may be processed before being provided to the side prediction engine module 148 and the key point location prediction engine module 150 to remove noise. The pressure readings may be digitally filtered by various digital signal processing techniques such as a finite impulse response (FIR) filter, Gaussian filter, smoothing, etc.

In some embodiments, the side prediction engine module 148 may apply a trained machine learning model that receives pressure data and outputs side predictions. In some embodiments, the side prediction engine module 148 may input, for each timestamp, a set of pressure data to the machine learning model. The machine learning model may output a probability for each possible side (e.g., prone, supine, left side, right side). Based on the output probabilities, the side prediction engine module 148 may select a side label associated with the highest probability. In some embodiments, the input of the machine learning model may include images or videos of the user sleeping on the weight support device 110 in addition to the pressure data. In some embodiments, the machine learning model may rely solely on the pressure data to make the prediction and to generate the user's figure. In some embodiments, images or videos of users may be used as training samples in training the machine learning model. The machine learning model, when fully trained, may not need to rely on images or videos of the users anymore.

Similarly, the key point location prediction engine module 150 may apply a trained machine learning model that receives pressure data and outputs key point locations of a user at different instances. Depending on the virtual model, there can be a predetermined number of joints (e.g., 14 joints), and the key point location prediction engine module 150 may output the key point locations as two-dimensional coordinates and a confidence probability between 0 and 1 for each key point location. The computer may then generate a skeleton of the user and determine the 2D spatial coordinates for the joints (e.g., the 14 joints) along with their probability. The example 14 joints may be hip, effector head, right shoulder, right forearm, right hand, left shoulder, left forearm, left hand, right thigh, right shin, right foot, left thigh, left shin, and left foot.

In some embodiments, the machine learning model may be unable to determine key point locations for one or more of the joints with a confidence probability greater than or equal to a confidence threshold. For example, when a user is lying on their left side with their right arm resting on the torso, the right side of the body is not in contact with the weight support device 110, so the key point location of the user's right shoulder, the right elbow, and the right wrist cannot be determined based on the pressure data. Accordingly, the output probabilities of the machine learning model for key point locations of the right shoulder, the right elbow, and the right wrist may be less than the confidence threshold. When one or more key point locations have a confidence probability that is less than the confidence threshold, the key point location prediction engine module 150 may predict the one or more key point locations for the user to be in a neutral or comfortable position based on observations in poses of historical users.

In one embodiment, the key point location prediction engine module 150 maintains a set of default key point locations for each type of joint. For each of one or more joints that do not satisfy the confidence threshold, the key point location prediction engine module 150 may use the default key point location for that joint. For example, continuing with the example of the user that is lying on the left side, the default key point locations for the shoulder joint, the elbow joint, and the wrist may be parallel to the torso and the default key point locations for the right leg may be stacked with the left leg. In some embodiments, the default key point locations are provided by an expert (e.g., a healthcare professional, sleep expert). In another embodiment, the default key point locations are determined by the computing server 140 by analyzing training data for the various machine learning models of the computing server 140 from most frequently occurring poses in the training data. The training data may include historical entries that each includes pressure data and key point locations for historical users.

In some embodiments, the key point location prediction engine module 150 predicts the key point locations of a limb that is not in contact with the weight support device 110 based on one or more of the predicted key point locations of another limb, the torso, and the head that are in contact with the weight support device 110. For example, referring again to the user that is lying on the left side, depending on whether the right leg is stacked on top of the left leg or the right leg is extended in front of the left leg and in contact with the weight support device 110, the predicted key point locations of the right arm may vary. The key point location prediction engine module 150 may input the key point locations with probabilities greater than the confidence threshold into a machine learning model that is trained to output predicted key point locations of the limb that is not in contact with the weight support device 110.

Figure 4:
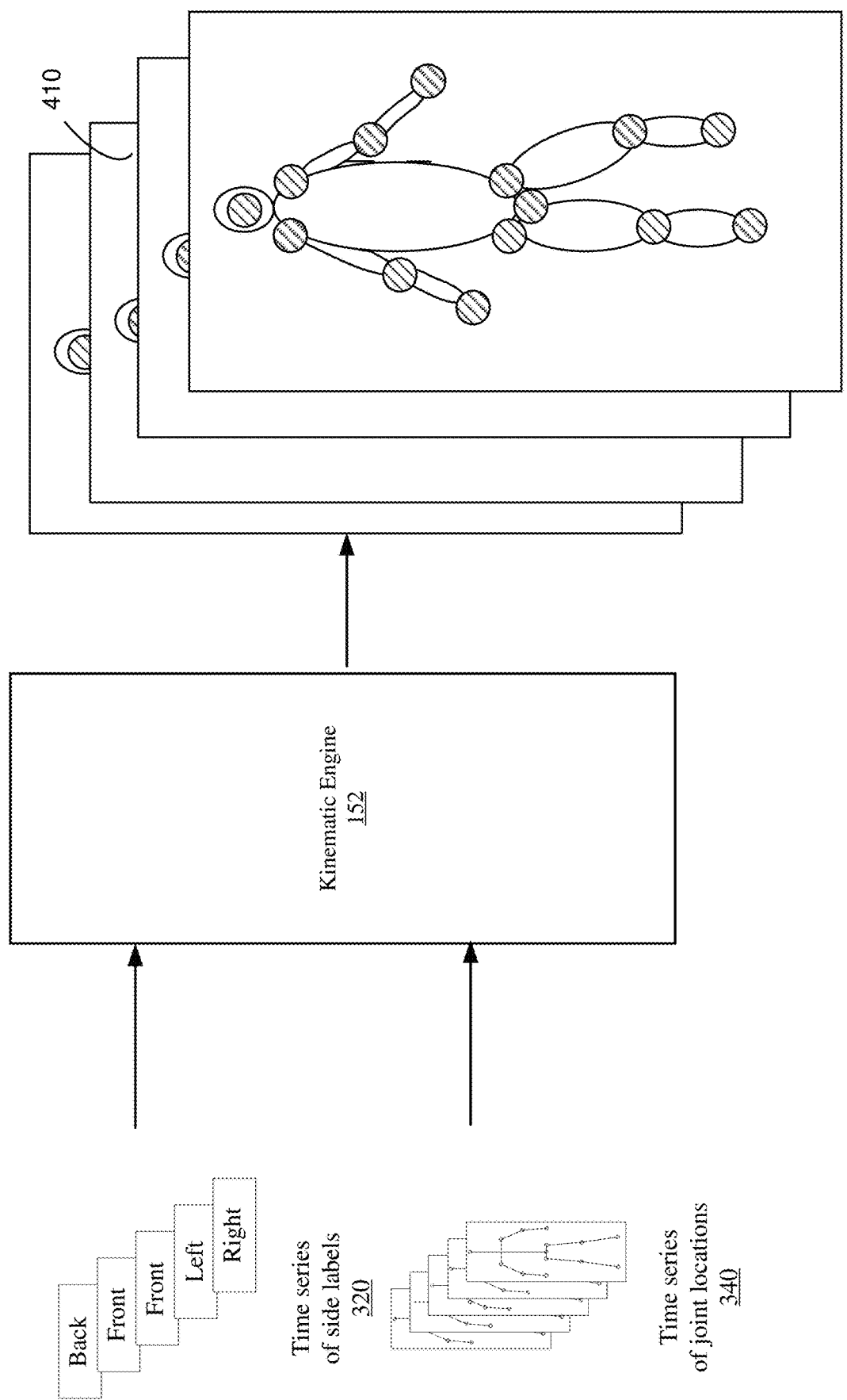
FIG. 4 is a conceptual diagram illustrating an example pipeline in the system consisting of a kinematic engine module for generating a virtual figure, in accordance with some embodiments.

FIG. 4 is a conceptual diagram illustrating an example computer-implemented process for generating a virtual figure, in accordance with some embodiments. The time series of side labels 320 and the time series of key point locations 340 may be provided as input to the kinematic engine module 152. The kinematic engine module 152 determines movements of one or more of the head representation, the torso representation, and the limb representation based on changes in the side labels and key point locations between timestamps. The kinematic engine module 152 is configured to iteratively determine how a user moves from one pose (which can be described by the key point locations) at a first timestamp to another pose at a next timestamp. In one embodiment, the kinematic engine module 152 uses inverse kinematics to determine angles of all of the joints and the path of trajectory based on the predicted key point locations and side label. The kinematic engine module 152 determines the angles between the torso representation, the one or more limb representations, and the head representations at various timestamps and provides the determined angles to the figure generation engine module 144 that updates the virtual figure 410.

Example Graphical User Interfaces

FIGS. 5A and 5B illustrate an example graphical user interface 500 displaying a virtual figure representing a user at two different time stamps, in accordance with some embodiments. A computer (e.g., the local computer 120, computing server 140, the user device 170) can display the graphical user interface (GUI) 500 that displays a video 510 of a virtual FIG. 540 corresponding to a user supported by the weight support device 110. The GUI 500 may include a timeline 530 with a slider 550 marking a timestamp of the displayed video frame. The slider 550 may be interacted with by a user and moved along the timeline 530 (e.g., dragged and dropped), allowing the user to select a particular timestamp of interest. A speed at which the video 510 of the virtual figure 540 is played may depend on the speed at which the slider 550 is moved. The GUI 500 may be an example of the interface 165 discussed in FIG. 1. At a particular timestamp, the GUI 500 may display information 520 related to the positioning (e.g., related to a pose) of the user, such as a side label.

As illustrated in FIG. 5A, at 3:15 am, the user was lying on their back with all of the limbs extending straight away from the torso (e.g., in a starfish position). Because all of the user's limbs were in contact with the weight support device 110, the key point location prediction engine module 150 is able to predict all the key point locations with a probability greater than the confidence threshold. In contrast, as illustrated in FIG. 5B, at 6:00 am, the user was lying on their left side with their left arm, left leg, and right leg in contact with the weight support device 110. However, the right arm was not in contact with the weight support device 110 so the pressure data measured by the weight support device 110 does not capture the position of the right arm. For key point locations associated with a probability less than the confidence threshold, the GUI 500 may visually distinguish a portion of the virtual figure 540. In FIG. 5B, the right arm 560 of the virtual figure 540 is illustrated with dotted lines while the rest of the virtual figure 540 is illustrated with solid lines.

The display of virtual figure 540 may be in synchronization with the movement of the user in real time. For example, in a health care facility, a plurality of patients may be monitored using the weight support device 110 in real time. Their corresponding virtual figures 540 may be displayed together in real time at a GUI 500 in a computer at a control room, such as the main nursing station. The GUI 500 may provide various alerts, such as potential fall positions, pose change reminders, ulcer monitoring and prevention along with the display of the virtual figures 540. In some embodiments, the virtual figure 540 may also be associated with a recording over a period of time (e.g., an entire night). The pose and sleeping quality of the user may be monitored and illustrated using the virtual figure 540 by replaying the movement of the virtual figure 540. The video of the virtual figure 540 may be fast forwarded or be played at a fast speed. Alternatively, or additionally, the summary of a user's sleeping condition may be presented as a series of frames that discretely shows the user's change of pose over the night and the timestamp when the user change a pose.

Figure 5C:
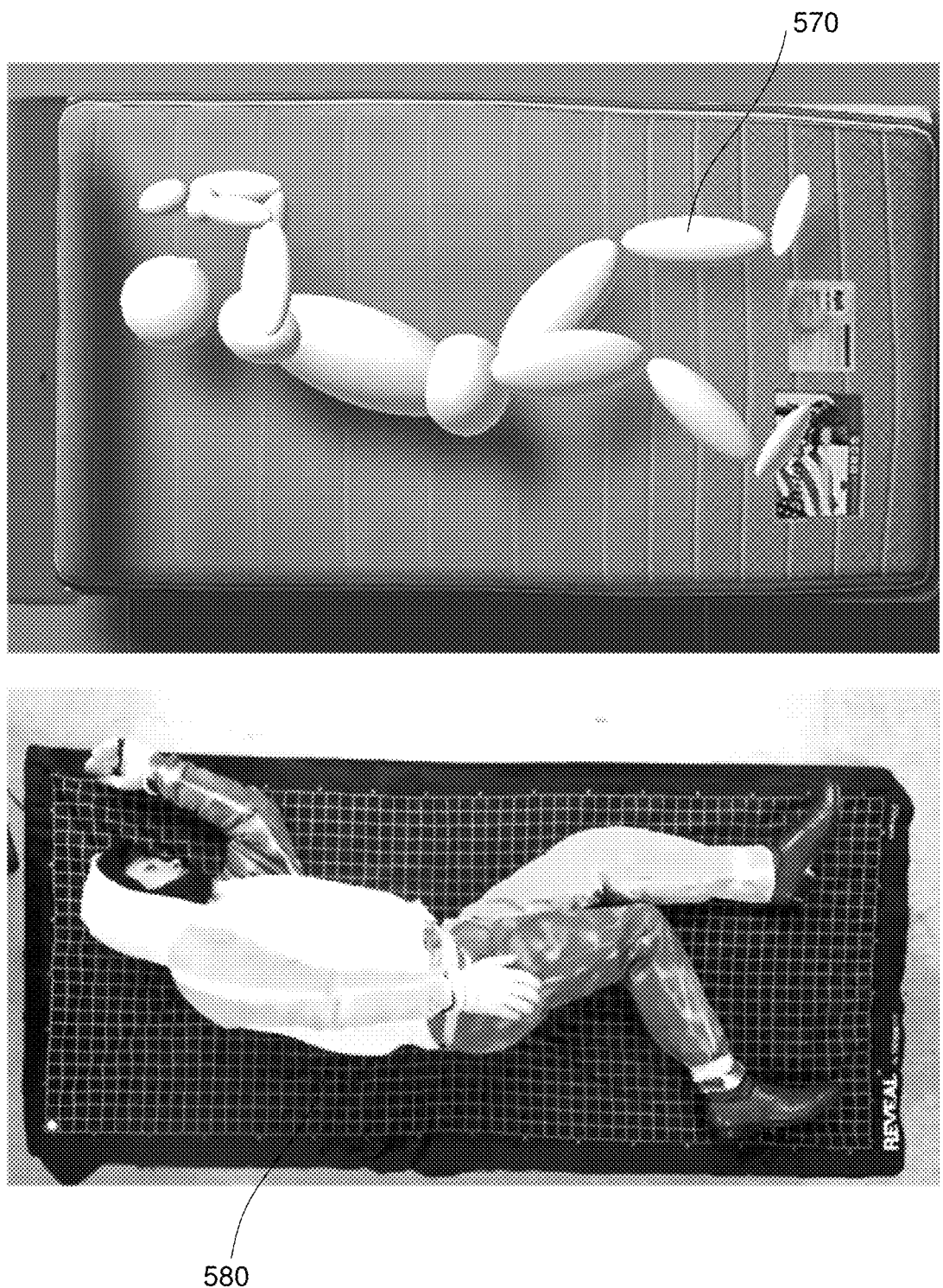
FIGS. 5C-5H illustrate a user and a virtual figure that is updated as the user moves, in accordance with some embodiments.
Figure 5D:
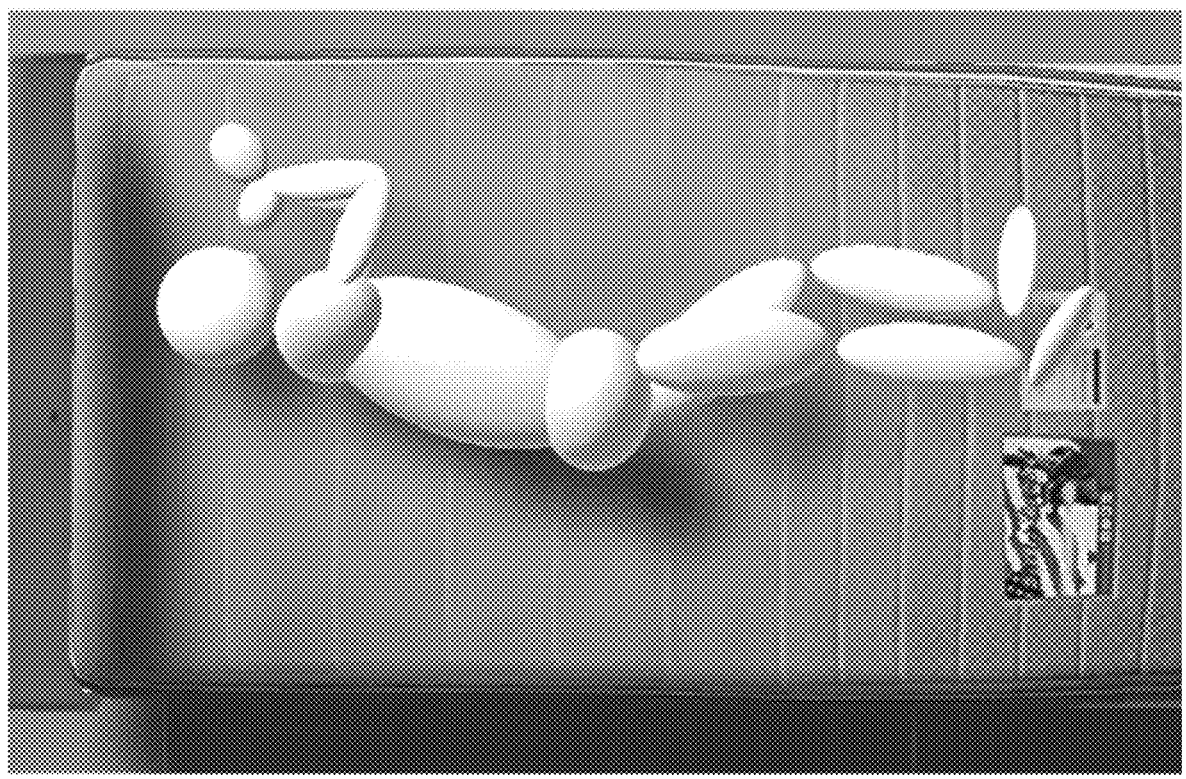
Figure 5D:
Figure 5E:
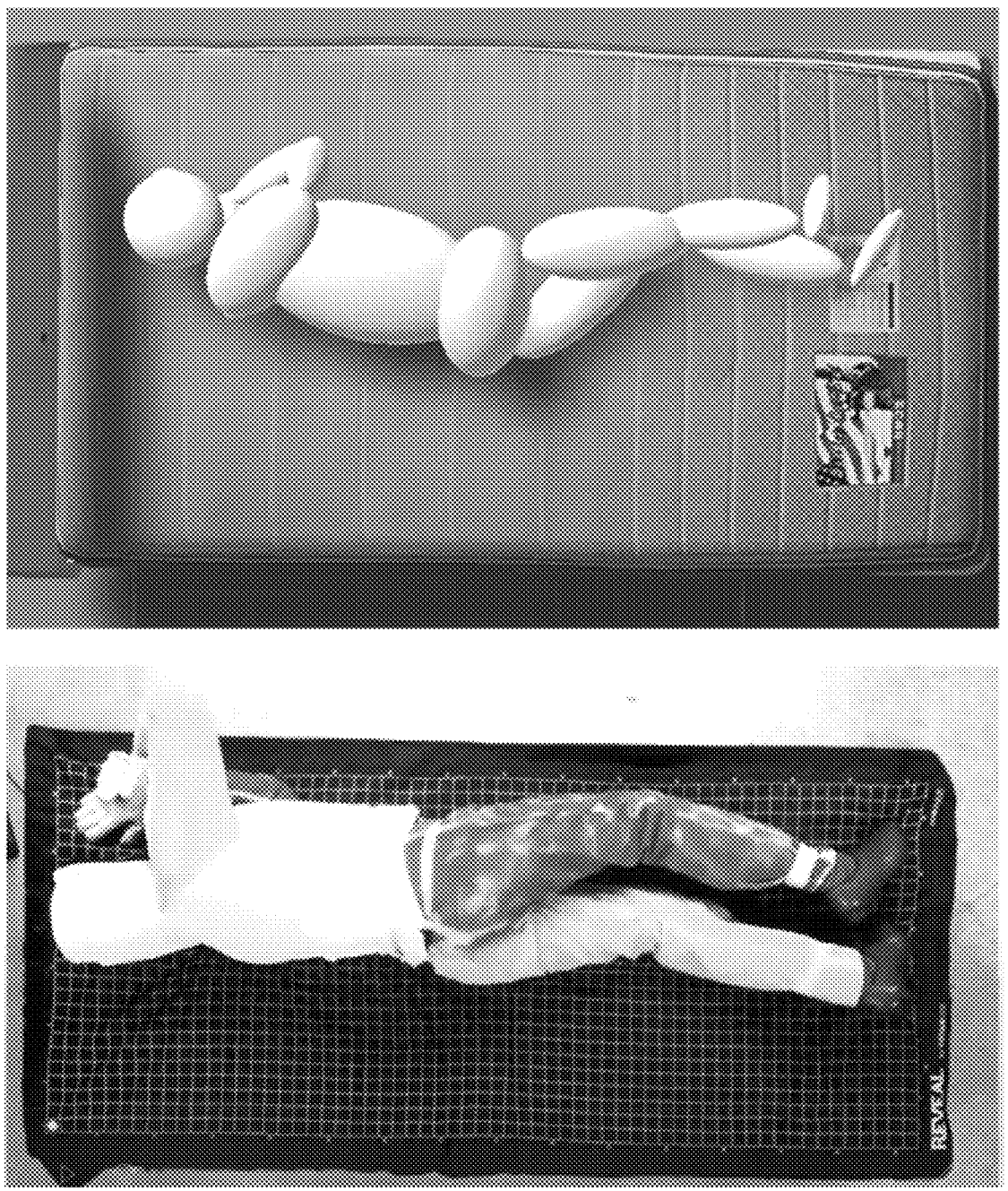
Figure 5F:
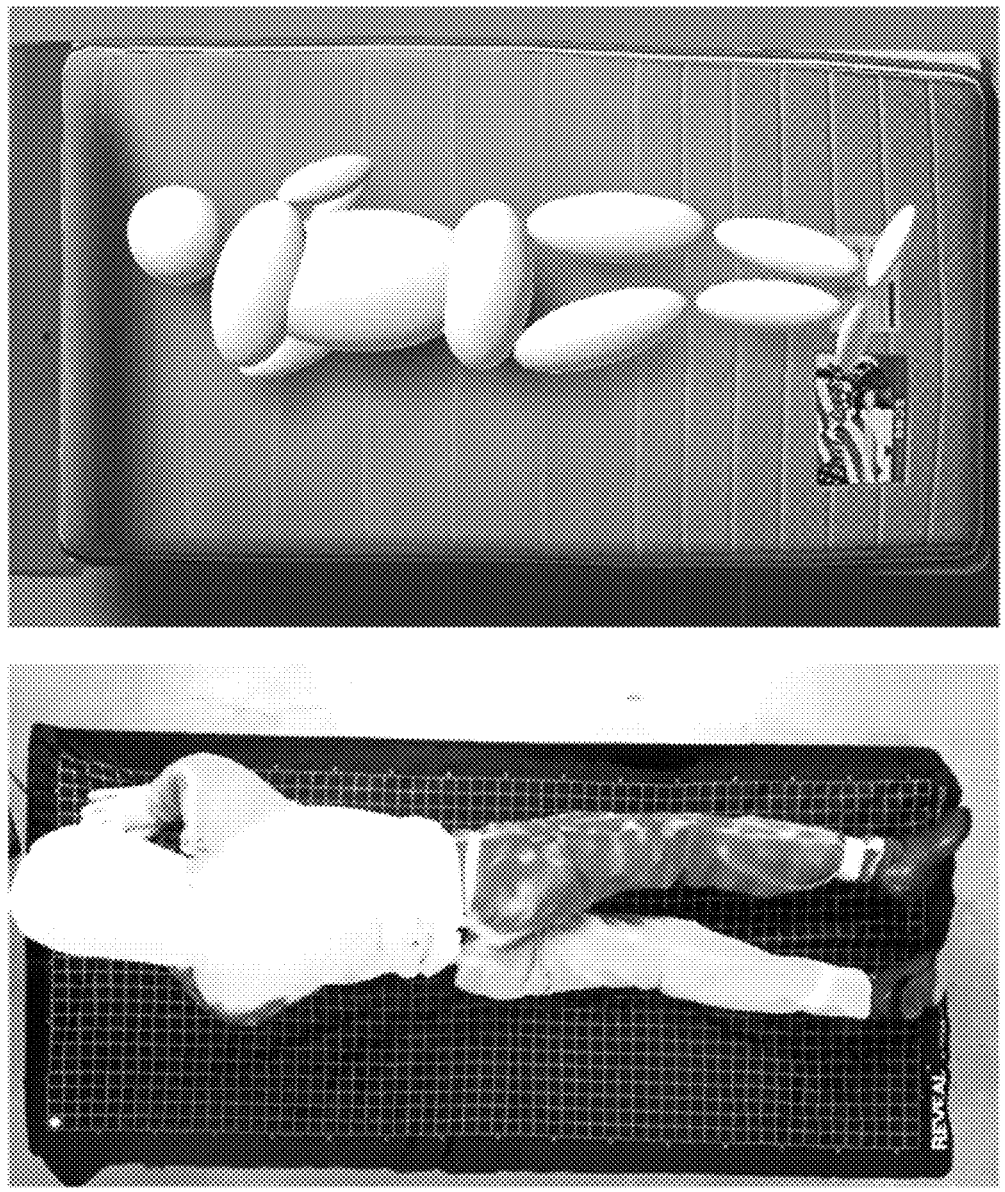
Figure 5G:
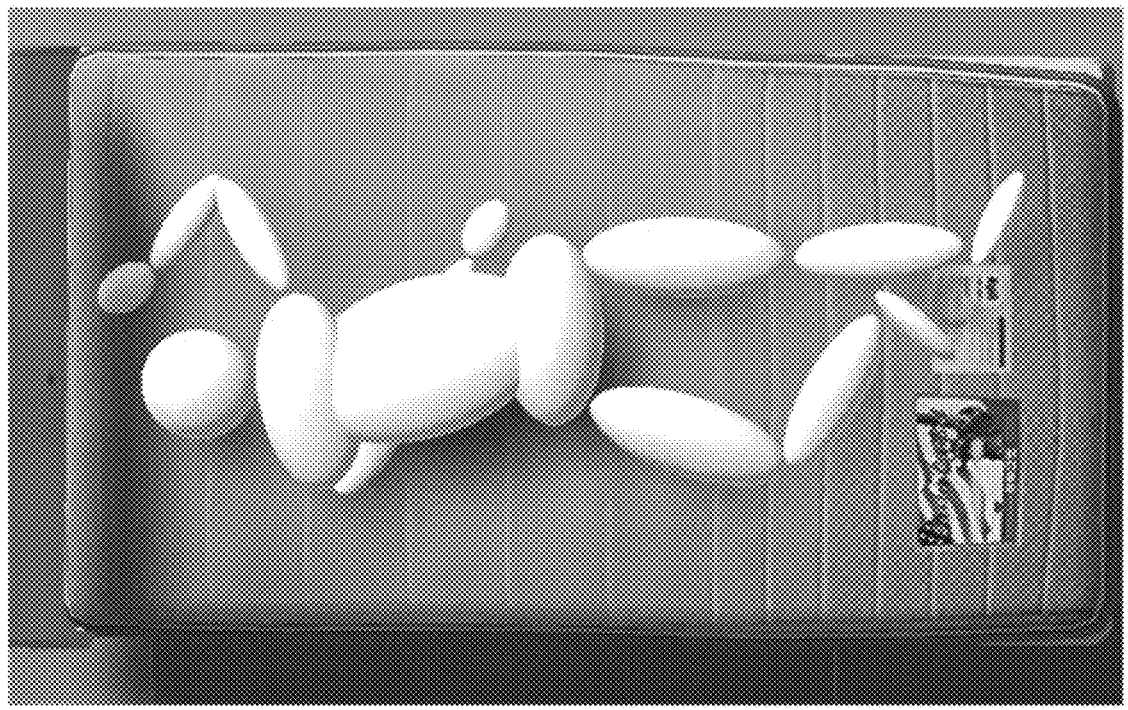
Figure 5G:
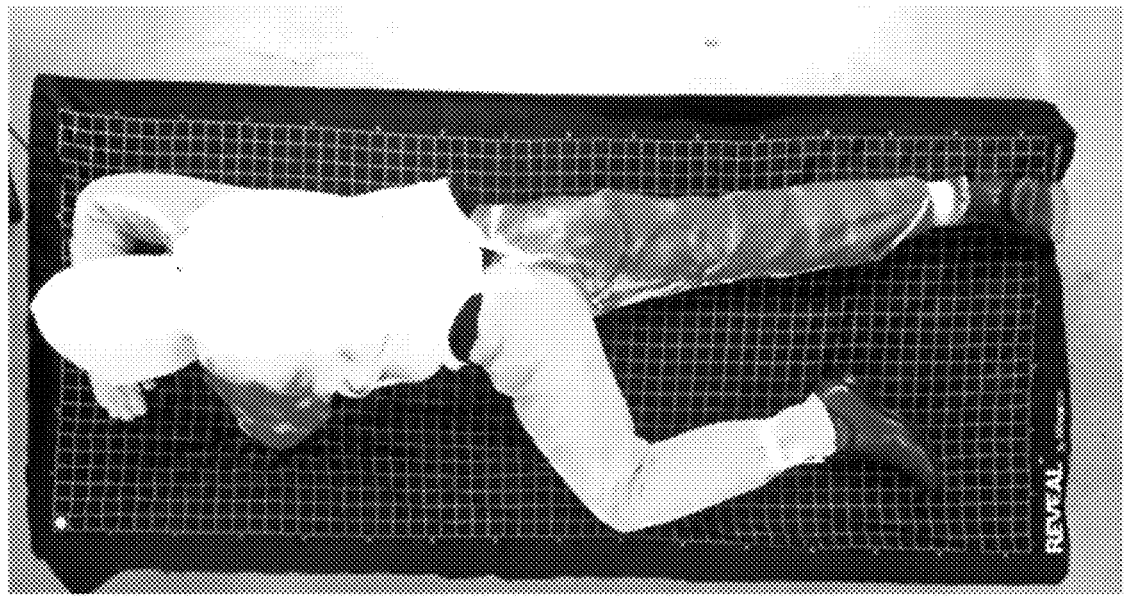
Figure 5H:
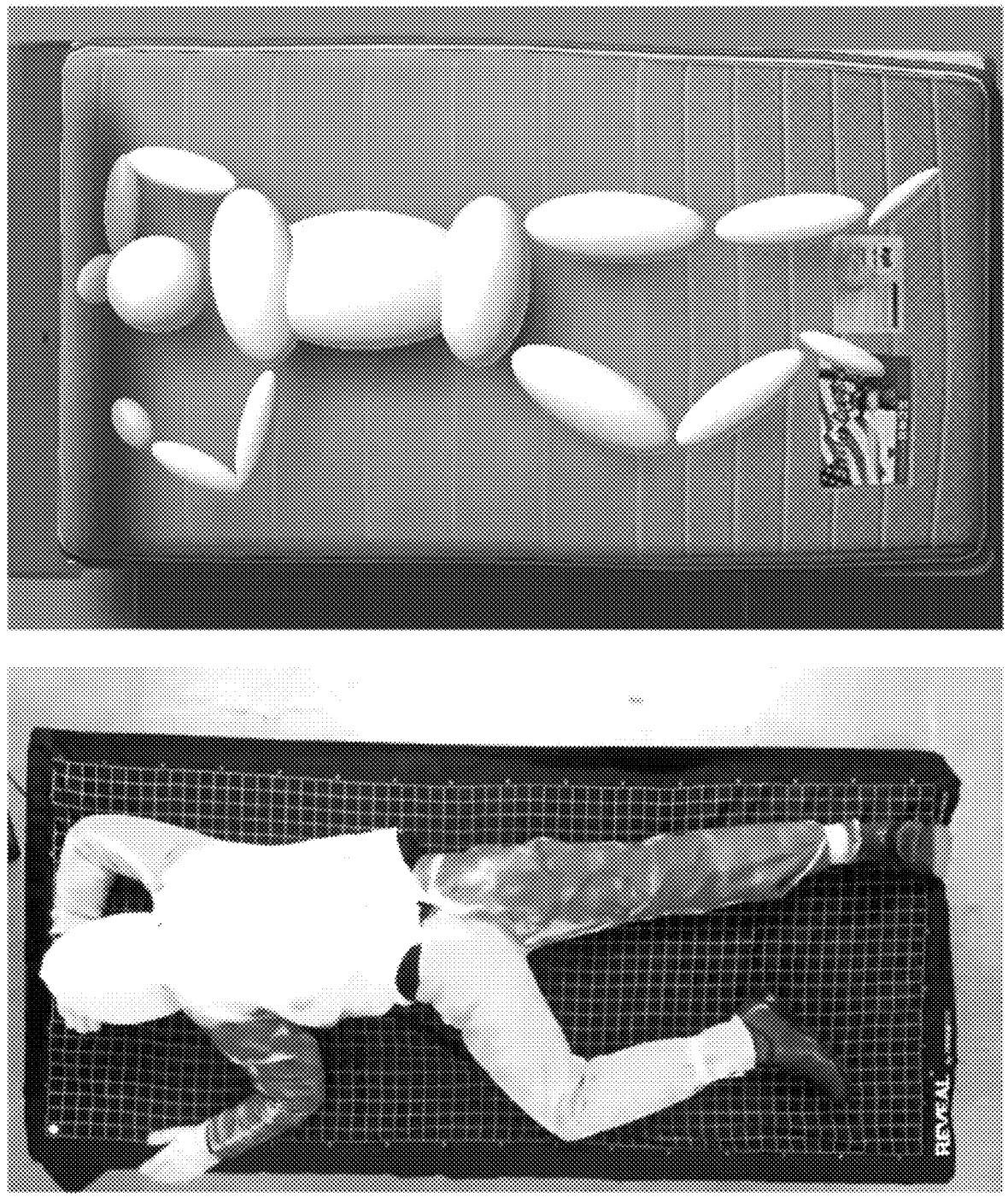

FIGS. 5C-5H illustrate a user 580 and a virtual figure 570 that is updated as the user 580 moves, in accordance with some embodiments. The virtual figure 570 may be updated in real-time in synchronization with the user 580 based on pressure data collected by the weight support device 110. Alternatively, or additionally, the user movement may be recorded by a camera and the virtual figure 570 may be replayed along with the video of the user movement. When pressure data is not available to determine key point locations of a body part, the key point locations are predicted for the user 580 to be in a neutral or comfortable position. For example, as illustrated in FIG. 5C, the user 580 is lying on the left side with the left arm in contact with the weight support device 110 and the right arm resting on the right side such that the right side is not in contact with the weight support device 110. Because weight support device 110 may not receive sufficiently definite pressure data with respect to the right arm, the position of the right arm is predicted based on the rest of the user's body that is in contact with the weight support device 110. In the example illustrated in FIG. 5C, the right arm is predicted to overlap with the left arm even though it is actually resting on the user's torso. Images of the user 580 are shown in FIGS. 5C-5H to demonstrate the synchronization of the user 580 and the virtual figure 570, but the images may not be used for the virtual figure 570 generation. While a video of a user is illustrated in FIG. 5C through 5H alongside with the virtual figure 570, in some embodiments, a camera is not available to capture the user. Instead, the system may rely solely on data generated by the sensors carried on the weight support device 110. In turn, only the virtual figure 570 is displayed and may be used as a representation of the user in a real-time synchronization manner.

Figure 5I:
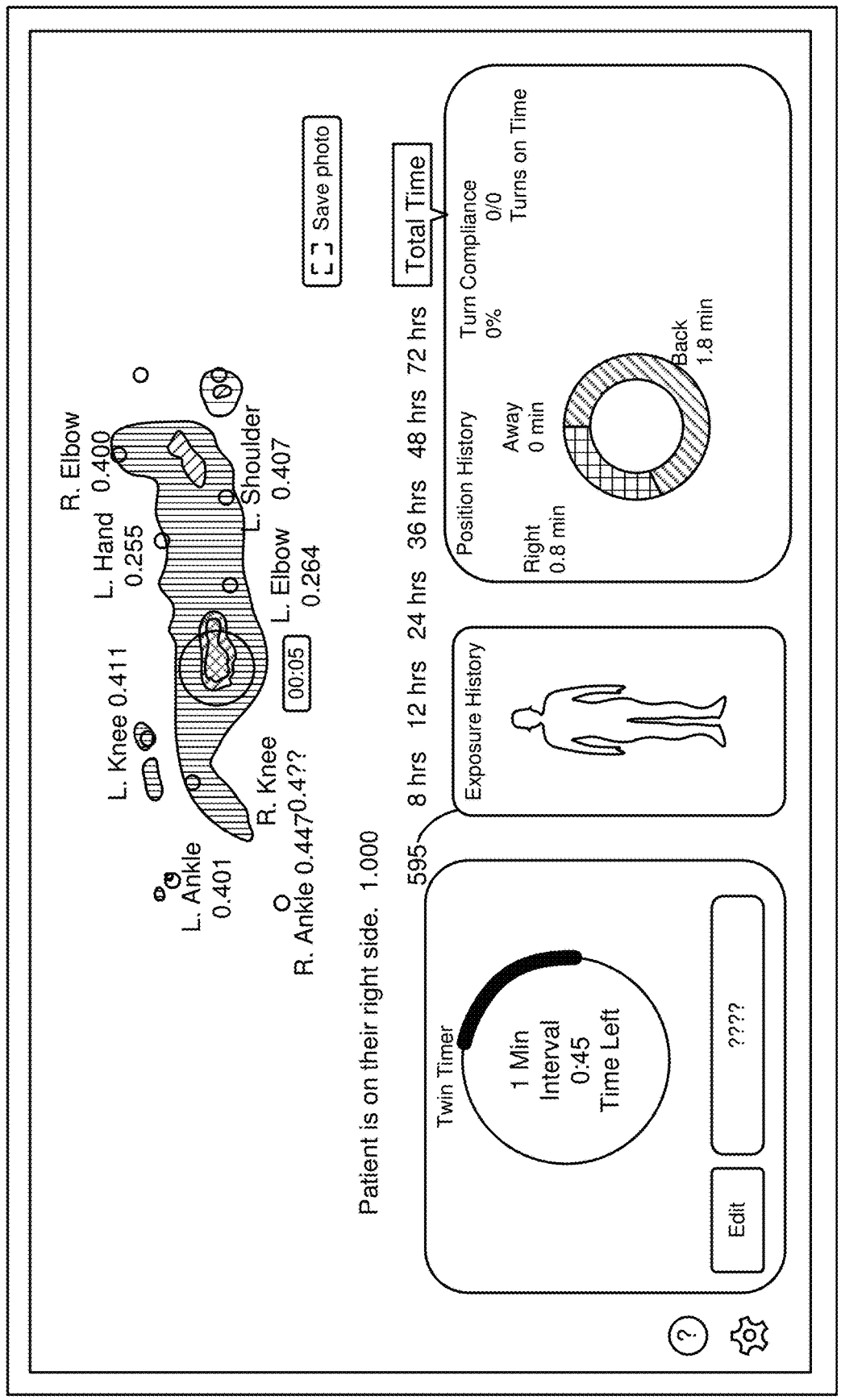
FIG. 5I illustrates an example graphical user interface used to track pressure exposure over time, in accordance with some embodiments.

FIG. 5I illustrates an example graphical user interface used to track pressure exposure over time, in accordance with some embodiments. In the graphical user interface, a heat map 590 illustrating the magnitude of the pressure data measured at various locations on the user's body (e.g., 0.447 at right ankle, 0.264 at left elbow). In some embodiments, the exposure history of pressure may be represented using a virtual figure 595 to highlight locations of the user's body that have a high risk of developing pressure injuries. Although not illustrated in FIG. 5I, the virtual figure 595 may be a three-dimensional model, and a user may interact with the virtual FIG. 595 by rotating the virtual figure 595, zooming in/out to view portions of the virtual FIG. 595 in more detail. In some embodiments, the heat map 590 of the pressure data may be projected onto the virtual figure 595 and change in real-time as the pressure data updates with user's movements or with previously recorded pressure data.

Figure 5J:
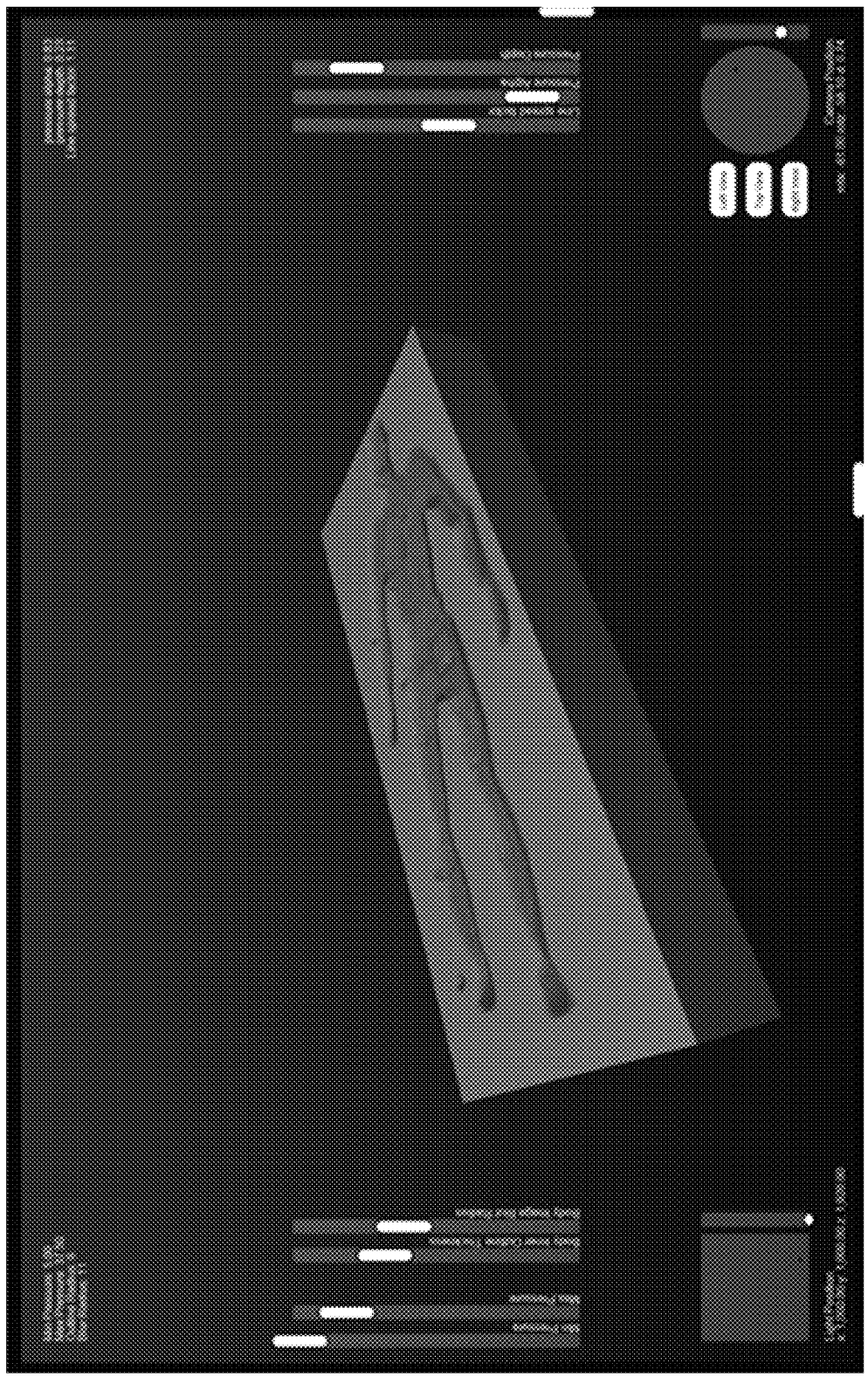
FIG. 5J illustrates an example visualization tool for impression made onto a surface of a weight support device, in accordance with some embodiments.

FIG. 5J illustrates an example visualization tool for impression made onto a surface of a weight support device, in accordance with some embodiments. The impression is another way of representing a user's body and can be used to show pressure points, accumulation of pressure over time, or locations on the user's body with high risk of developing injuries. In the example illustrated in FIG. 5J, the weight support device is a mattress, and the visualization tool shows an impression of a user on their back. The process for generating the impression is described below with respect to FIG. 6B.

Example Virtual Figure Rendering Process

Figure 6A:
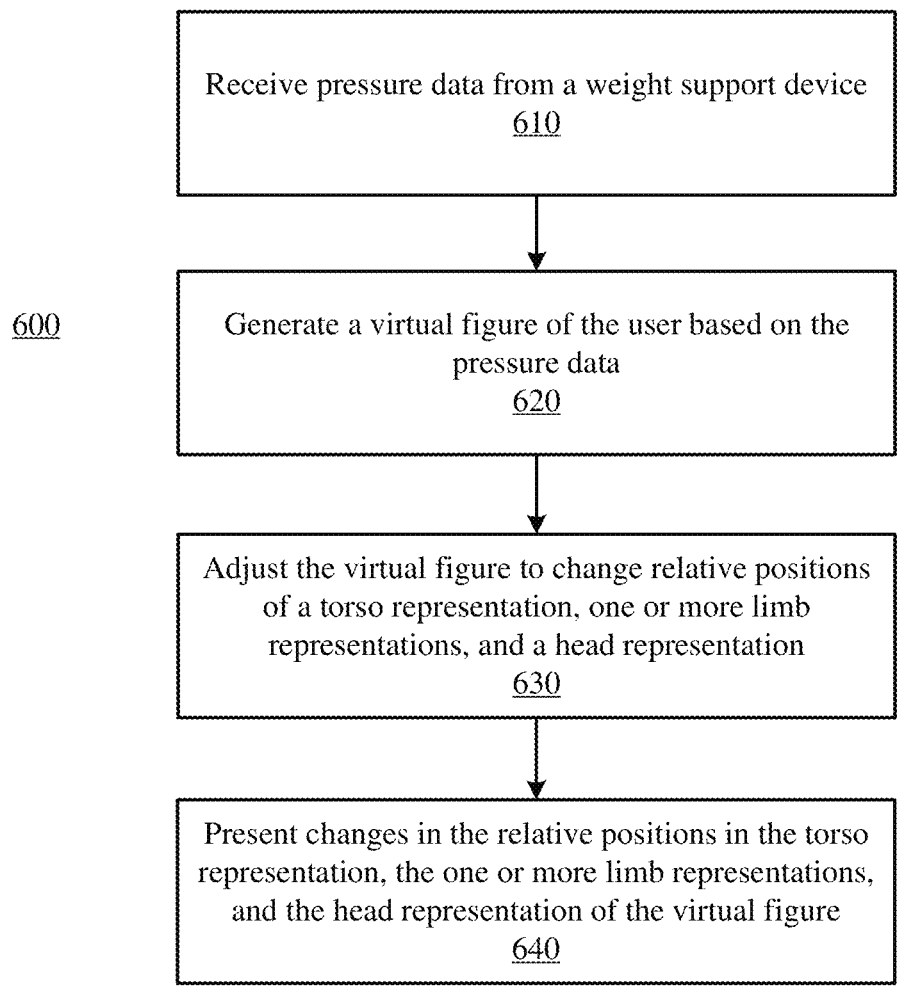
FIG. 6A is a flowchart depicting an example process for generating a virtual figure, in accordance with some embodiments.

FIG. 6A is a flowchart depicting an example process 600 for generating a virtual figure, in accordance with some embodiments. During the process 600, a computer receives 610 pressure data from a weight support device that supports a user during a measurement period. The weight support device includes a sensor grid with a plurality of sensors that measure pressure data. The user may lie down and move relative to the weight support device causing pressure readings measured by the plurality of sensors to change according to the user's movements.

Based on the pressure data, the computer generates 620 a virtual figure (2D or 3D). In some embodiments, the computer may scale the virtual figure according to the characteristics of the user's body. The scaling of the virtual figure can be performed globally based on the user's weight and height. Alternatively, or additionally, portions of the virtual figure (e.g., specific segment or limb) may be scaled locally based on the physical profile of the user such as the body ratio. The scaling may be performed based on a machine learning model that receives the physical profile of the user and outputs parameters for the virtual figure. The physical profile may be manually entered by the user and/or may be generated based on pressure data measured by the weight support device 110. For example, the weight support device 110 can collect sufficient pressure data to determine most, if not all, key point locations of the user's body when the user is lying in an upright position such that all of the user's body is in contact with the weight support device. Based on the key point locations and/or weight measured by the weight support device, the computer can estimate the user's body size for scaling the virtual figure.

The computer may generate the virtual figure using a dynamic model including objects corresponding to body segments connected by hinges that have constraints defining degrees of movement of the objects. An object represents a rigid body (e.g., head, forearm, upper arm, torso) with a mass, dimension, physical boundary (colliders), and material (friction), and the dynamic model simulates the object's rotation and transition when a force is applied to it. To create the virtual figure, multiple objects (e.g., represented by 3D ellipses) with specified mass, dimension, collider, and friction are connected together with hinges. An object's scale, size, and/or the assigned mass may be proportional to the user's BMI estimated by the key point locations determined from the pressure data. Hinges have a set rotation range in different directions and dynamic characteristics to mimic the normal range of motion in a human's body. For example, arms cannot rotate back more than 20 degrees because of the shoulder joint range of motion and the head cannot rotate to the sides more than 100 degrees. By determining the range of motion for each object connected to one or more hinges, the computer can generate a virtual figure that accurately mimics the dynamics of a human body. The computer determines how to represent the virtual figure to act similar to the human body in response to any applied force (e.g., user adjusting their body position) using the dynamic model to calculate the movements of the objects representative of the user's body segments.

The virtual figure may include a torso representation, one or more limb representations, and a head representation. The virtual figure may be a 3-dimensional figure representative of the user. The relative positions of the torso representation, the one or more limb representations, and the head representation are determined based on the pressure data. For each timestamp (e.g., every second) during the measurement period, the computer may predict which side of the user was in contact with the weight support device and key point locations of the user's body based on the pressure data. The predicted key point locations may be two dimensional coordinates, but when the predicted key point locations and side are provided to a kinematic model, the kinematic model determines angles of the joints and the movement of the joints.

In some embodiments, the key point locations and the side are determined using machine learning models. A deep learning key point location classification model may be trained to predict 2D locations of key point locations of the user's body (e.g., joint locations, center of mass of body parts) based on pressure data collected when the user is on the weight support device. A deep learning side classification model may be trained to predict the side of the user that is in contact with the weight support device. The predicted key point locations output from the key point location classification model represent desired locations for key point locations on the virtual figure. When a time series of key point locations and side predictions are provided to the kinematic model, the kinematic model determines angles of the joints at different times and determines rotational motion of the user given the range of motion of the joints. Because the pressure measurements are made on a 2D surface of the weight support device, the key point locations are limited to 2D predictions. However, because the kinematic model uses additional information such as range of motion of the joints, body part collisions, and friction, the 3D pose of the user can be predicted and represented through the virtual figure, which can be a 3D figure.

The computer adjusts 630 the virtual figure to change relative positions of the torso representation, the one or more limb representations, and the head representations based on the movement determined by the kinematic model. For example, the computer may continuously monitor the coordinates of various key point locations of the user based on the pressure data. When all key point locations are detected by the pressure sensors, the computer can update the virtual figure based on the coordinates of the key point locations, the dynamic model, and the kinetic model. For example, a key point movement may be continuously tracked by the weight support device 110. The computer can reflect the gradual change in coordinates of the key point by moving the object in the dynamical model accordingly. The key point locations define key coordinates of the objects in the dynamical model and the rest of the objects (e.g., thing that is between two key points) in the dynamical model may be interpolated. When one or more key point locations are missing, the computer may use a prediction engine module to predict the whereabout of the key point locations. For example, if the missing key point is between two other key points that are currently detected, the computer may predict the location of the missing key points based on natural posture of human, coordinates of the two other key points, interpolation, and constraints defined by human body joints.

The computer presents 640 the changes in the relative positions in the torso representation, the one or more limb representations, and the head representation of the virtual figure. The virtual figure may be presented as a video through a graphical user interface to provide a visual representation of the user's movements during the measurement period without capturing images of the user. Examples of the presentation are illustrated in FIG. 5A through FIG. 5H.

Figure 6B:
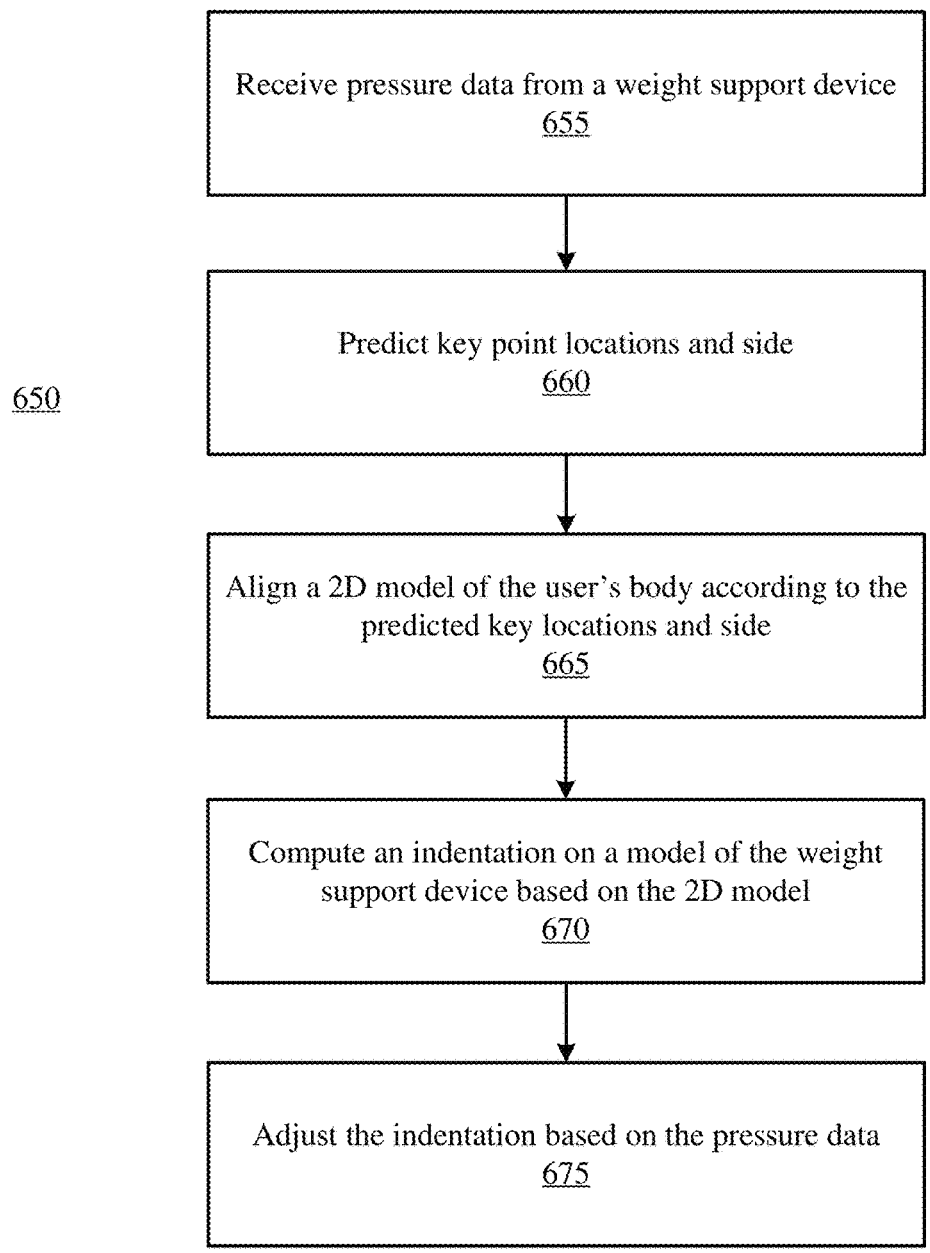
FIG. 6B is a flowchart depicting an example process for generating an impression, in accordance with some embodiments.

FIG. 6B is a flowchart depicting an example process for generating an impression, in accordance with some embodiments. During the process 650, a computer receives 655 pressure data from a weight support device that supports a user during a measurement period. The computer provides the pressure data as input to machine learning models that predict 660 key point locations measured by the weight support device and the side of the user that is in contact with the weight support device. The predicted key point locations measured by the weight support device and the side of the user indicate a pose of the user. The predicted key point locations measured by the weight support device and the side are aligned 665 with a 2D virtual figure model that may be generated using the process 600. For example, the alignment may include alignment of the key points measured by the weight support device to the key points in the virtual figure. The 2D virtual model may be scaled based the user's body features (e.g., height, weight, length of limbs). The alignment may generate a silhouette that overlays the surface of the weight support device. The outline of the silhouette may serve as the outline of the 2D virtual figure projected to the surface.

The computer generates a 3D model of the weight support device and computes 670 an indentation on the 3D model of the weight support device based on the 2D model of the user's body including the silhouette. The indentation may be initially generated by assuming that there is maximum deformation in the 3D model of the weight support device where it overlaps with the 2D model representation. To generate a more realistic impression, a gaussian blur may be applied around edges of the impression. The computer further adjusts 675 the indentation in the 3D model of the weight support device by overlaying the pressure data over the indentation and adjusting depth of the indentation at different locations in the indentation based on the pressure values detected at the different locations.

Example Key Point Location Prediction Process

Figure 7:
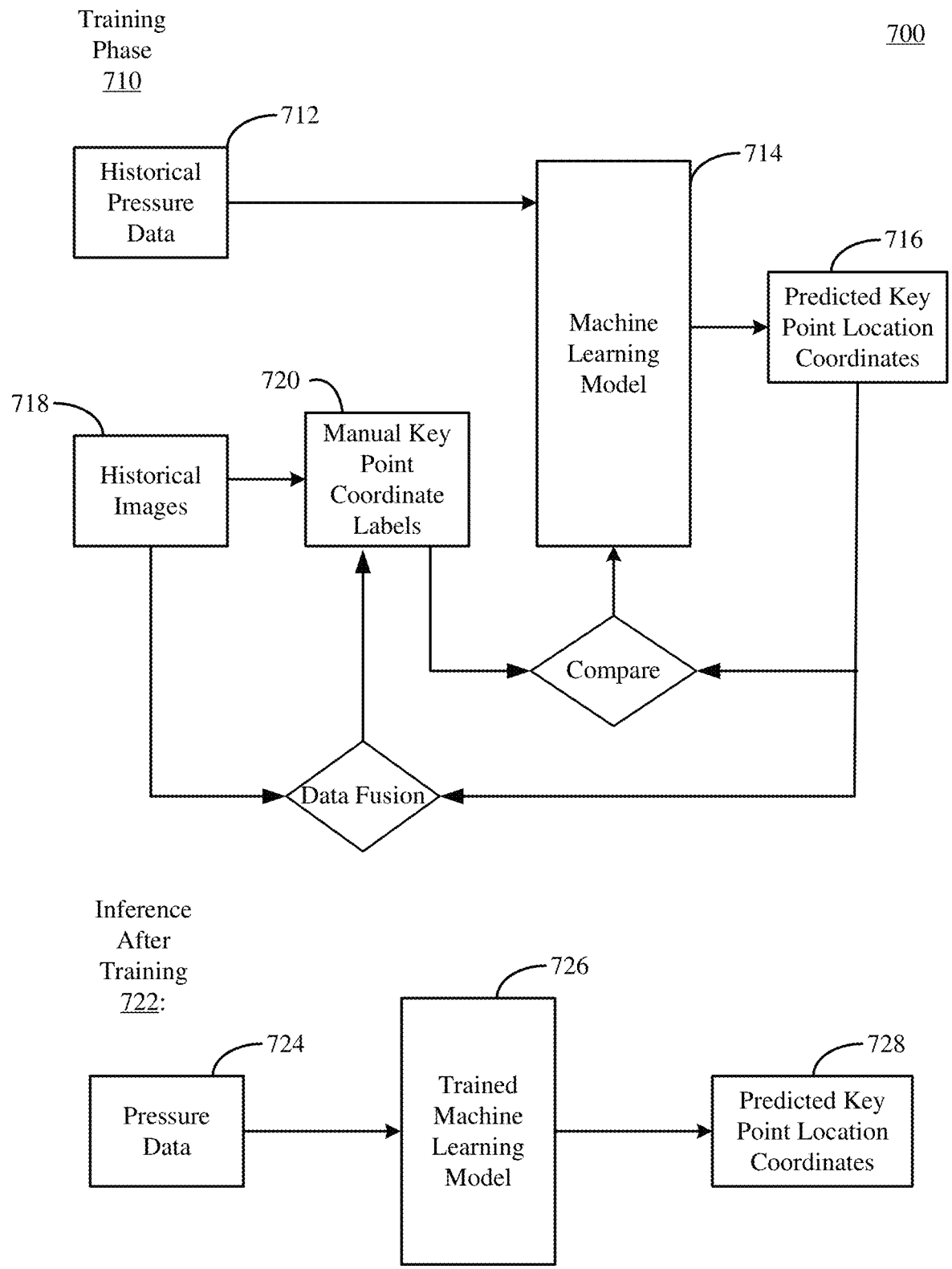
FIG. 7 is a flowchart depicting an example process for making key point location predictions for a limb not represented in pressure sensor readings, in accordance with some embodiments.

FIG. 7 is a flowchart depicting an example process 700 for making key point location predictions for a key point that is not represented in pressure sensor readings, in accordance with some embodiments. The process 700 may be used to supplement the data and results determined at step 620 and step 630 of process 600 for making key point location predictions of missing key points. In some cases, the pose of the user may affect the detection of certain key point locations by the pressure sensor. For example, when a user is lying on their left side with their right arm resting on the torso, the right side of the body is not in contact with the weight support device 110, so the key point location of the user's right shoulder, the right elbow, and the right wrist cannot be determined based on the pressure data. The process 700 is an example how the coordinates of missing key point locations may be predicted.

During a training phase 710, a machine learning model 714 is trained to predict key point location coordinates 728 based on input pressure data 724. The machine learning model 714 is trained using historical pressure data 712 collected by weight support devices during historical measurement periods and corresponding historical images 718 of users on the weight support devices captured during the historical measurement periods by image sensors such as cameras. The historical images 718 are annotated with manual key point coordinate labels 720 that provide coordinates of the key point locations. When the historical pressure data 712 collected when a portion of a user's body is not in contact with the weight support device, the historical pressure data 712 is missing information for one or more key point locations. However, the missing key point locations can be provided by the corresponding historical image 718 that is annotated with the coordinates of the missing key point locations. For example, a historical image 718 of a user may be manually annotated to identify missing and other key point locations of the user. In some embodiments, the predicted key point location coordinates 716 output by the machine learning model 714 based on the historical pressure data 712 and predicted key point location coordinates 716 generated by applying one or more object recognition machine learning models on the historical images 718 may be combined and provided to human annotators. The human annotators may review the combined predicted key point location coordinates 716 initially determined by machine-learning models and adjust the machine-learning based predictions as needed to provide the manual key point coordinate labels 720, which is more efficient than the annotators providing every key point location coordinate label 720 by reviewing raw historical pressure data 712 and raw historical images 718. Alternatively, or additionally, one or more object recognition machine learning models may be used to analyze the historical image 718 and automatically annotate the key point locations for the manual key point coordination labels 720.

When the historical pressure data 712 is provided as input to the machine learning model 714, the machine learning model 714 predicts key point location coordinates 716. The predicted key point location coordinates 716 are compared to the key point location coordinate labels 720 that are generated, for example, by the historical images 718. Based on the comparison between the predicted key point location coordinates 716 and the key point location coordinate labels 720 associated with the historical images 718, weights of the machine learning model 714 may be adjusted iteratively to improve the predictability of the machine learning model 714. The historical pressure data 712 may not include pressure data for one or more key point locations, but the machine learning model 714 learns to predict the key point location coordinates 716 for the missing key point locations based on historical images 718. After the machine learning model 714 has been trained, the trained machine learning model 726 can be deployed to make inferences 722 of key point location coordinates 728 based on only pressure data 724. In some embodiments, the weight support device does not need to be paired with a camera system. Because the trained machine learning model does not necessarily need images, the weight support device 110 does not need to be paired with a camera system, which can reduce the cost of the weight support device 110 and improve security. Further, the trained machine learning model does not analyze image data after being deployed, so the key point location coordinates and the side can be predicted with less time and computational resources.

Other example processes that may be used in place of or in addition to the process 700 are described above with reference to key point location prediction engine module 150.

Example Architecture of Machine Learning Models

In various embodiments, a wide variety of machine learning models may be used in the side prediction engine module, key point location prediction engine module, fall outcome prediction engine module, sleep quality prediction engine module, seizure prediction engine module, and other modules for other uses described herein. The machine learning models include but are not limited to decision trees, decision forests, support vector machines (SVMs), regression models, Bayesian networks, genetic algorithms, and deep learning models. The machine learning models may be trained using different methods including but not limited to supervised learning, unsupervised learning, self-supervised learning, and semi-supervised learning. Deep learning models that may also be used include but not limited to neural networks, including fully-connected neural networks, spiking neural networks, convolutional neural networks (CNN), deep belief networks, Boltzmann machines, autoencoder networks, and recurrent neural networks (RNN) (e.g., long short-term memory networks (LSTM)), and transformer neural networks. For example, for the side prediction engine module 148 and the key point location prediction engine module 150 that is described in FIG. 3 and the machine learning model used in process 700, a neural network may be used.

Figure 8:
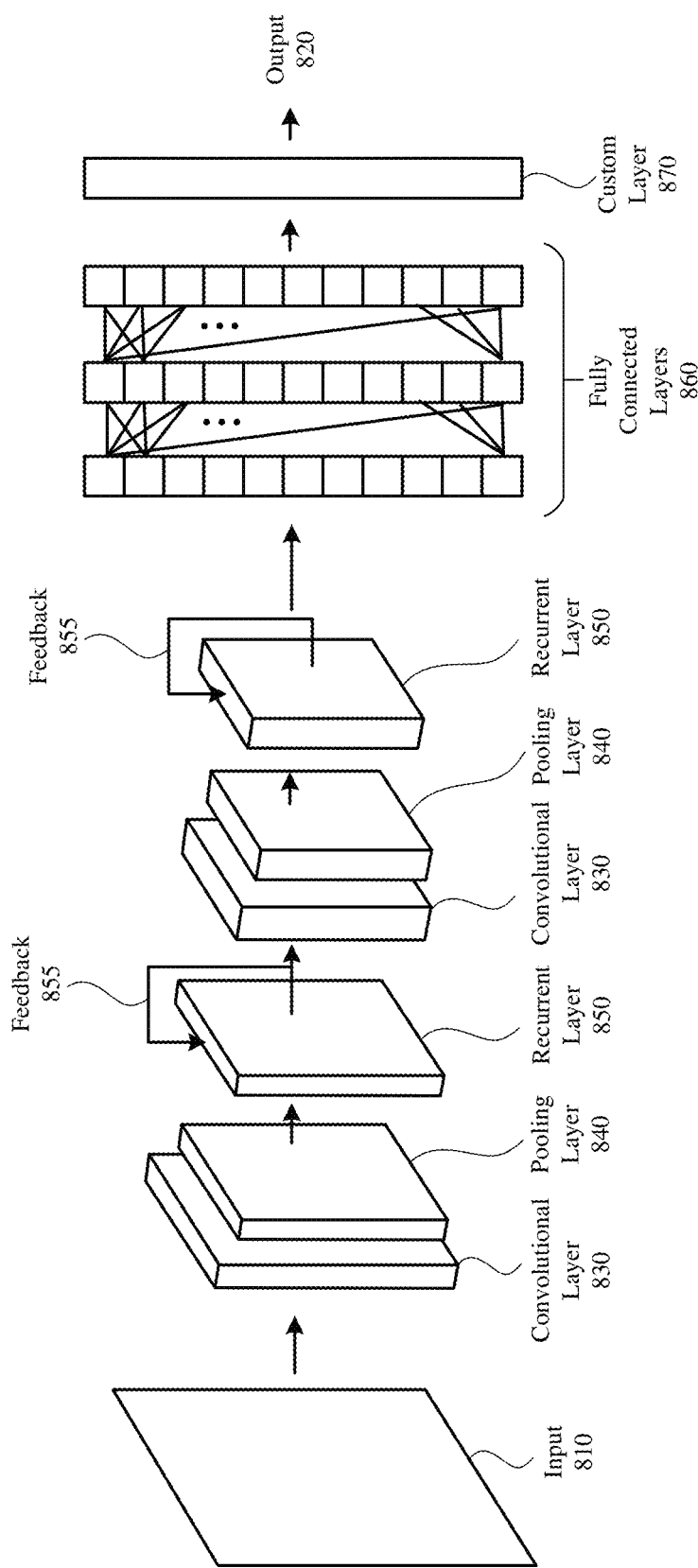
FIG. 8 is an example structure of a machine learning model, in accordance with some embodiments.

FIG. 8 shows an example structure of a neural network, which may include layers that may present in various machine learning models. For example, a CNN may include the convolutional layers and the pooling layers shown in FIG. 8. An LSTM may include the recurrent layers shown in FIG. 8. Each machine learning models may have its own structure and layers (while omitting some layers in FIG. 8). The order of the layers in FIG. 8 is also an example. The order of layers may change, depending on the type of machine learning model used.

Referring to FIG. 8, a structure of an example neural network (NN) is illustrated, according to an embodiment. The NN 800 may receive an input 810 and generate an output 820. The NN 800 may include different kinds of layers, such as convolutional layers 1230, pooling layers 840, recurrent layers 850, full connected layers 860, and custom layers 870. A convolutional layer 1230 convolves the input of the layer (e.g., an image) with one or more kernels to generate different types of images that are filtered by the kernels to generate feature maps. Each convolution result may be associated with an activation function. A convolutional layer 1230 may be followed by a pooling layer 840 that selects the maximum value (max pooling) or average value (average pooling) from the portion of the input covered by the kernel size. The pooling layer 840 reduces the spatial size of the extracted features. In some embodiments, a pair of convolutional layer 1230 and pooling layer 840 may be followed by a recurrent layer 850 that includes one or more feedback loop 855. The feedback 855 may be used to account for spatial relationships of the features in an image or temporal relationships of the objects in the image. The layers 830, 840, and 850 may be followed in multiple fully connected layers 860 that have nodes (represented by squares in FIG. 8) connected to each other. The fully connected layers 860 may be used for classification and object detection. In one embodiment, one or more custom layers 870 may also be presented for the generation of a specific format of output 820. For example, a custom layer may be used for image segmentation for labeling pixels of an image input with different segment labels.

The order of layers and the number of layers of the NN 800 in FIG. 8 is for example only. In various embodiments, a NN 800 includes one or more convolutional layers 1230 but may or may not include any pooling layer 840, recurrent layer 850, or fully connected layers 860. If a pooling layer 840 is present, not all convolutional layers 1230 are always followed by a pooling layer 840. A recurrent layer may also be positioned differently at other locations of the CNN. For each convolutional layer 830, the sizes of kernels (e.g., 3×3, 5×5, 7×7, etc.) and the numbers of kernels allowed to be learned may be different from other convolutional layers 830.

A machine learning model may include certain layers, nodes, kernels and/or coefficients. Training of a neural network, such as the NN 800, may include forward propagation and backpropagation. Each layer in a neural network may include one or more nodes, which may be fully or partially connected to other nodes in adjacent layers. In forward propagation, the neural network performs the computation in the forward direction based on outputs of a preceding layer. The operation of a node may be defined by one or more functions. The functions that define the operation of a node may include various computation operations such as convolution of data with one or more kernels, pooling, recurrent loop in RNN, various gates in LSTM, etc. The functions may also include an activation function that adjusts the weight of the output of the node. Nodes in different layers may be associated with different functions.

One or more machine learning models described herein may bear the structure described in FIG. 8. Example machine learning models include side prediction engine module 148, key point location prediction engine module 150, and machine learning model 726.

Each of the functions in the neural network may be associated with different coefficients (e.g. weights and kernel coefficients) that are adjustable during training. In addition, some of the nodes in a neural network may also be associated with an activation function that decides the weight of the output of the node in forward propagation. Common activation functions may include step functions, linear functions, sigmoid functions, hyperbolic tangent functions (tanh), and rectified linear unit functions (ReLU). After an input is provided into the neural network and passes through a neural network in the forward direction, the results may be compared to the training labels or other values in the training set to determine the neural network's performance. The process of prediction may be repeated for other images in the training sets to compute the value of the objective function in a particular training round. In turn, the neural network performs backpropagation by using gradient descent such as stochastic gradient descent (SGD) to adjust the coefficients in various functions to improve the value of the objective function.

Multiple rounds of forward propagation and backpropagation may be performed. Training may be completed when the objective function has become sufficiently stable (e.g., the machine learning model has converged) or after a predetermined number of rounds for a particular set of training samples. The trained machine learning model can be used for side prediction, key point location prediction, fall outcome prediction, sleep quality prediction, seizure prediction, or another suitable task for which the model is trained.

Computing Machine Architecture

Figure 9:
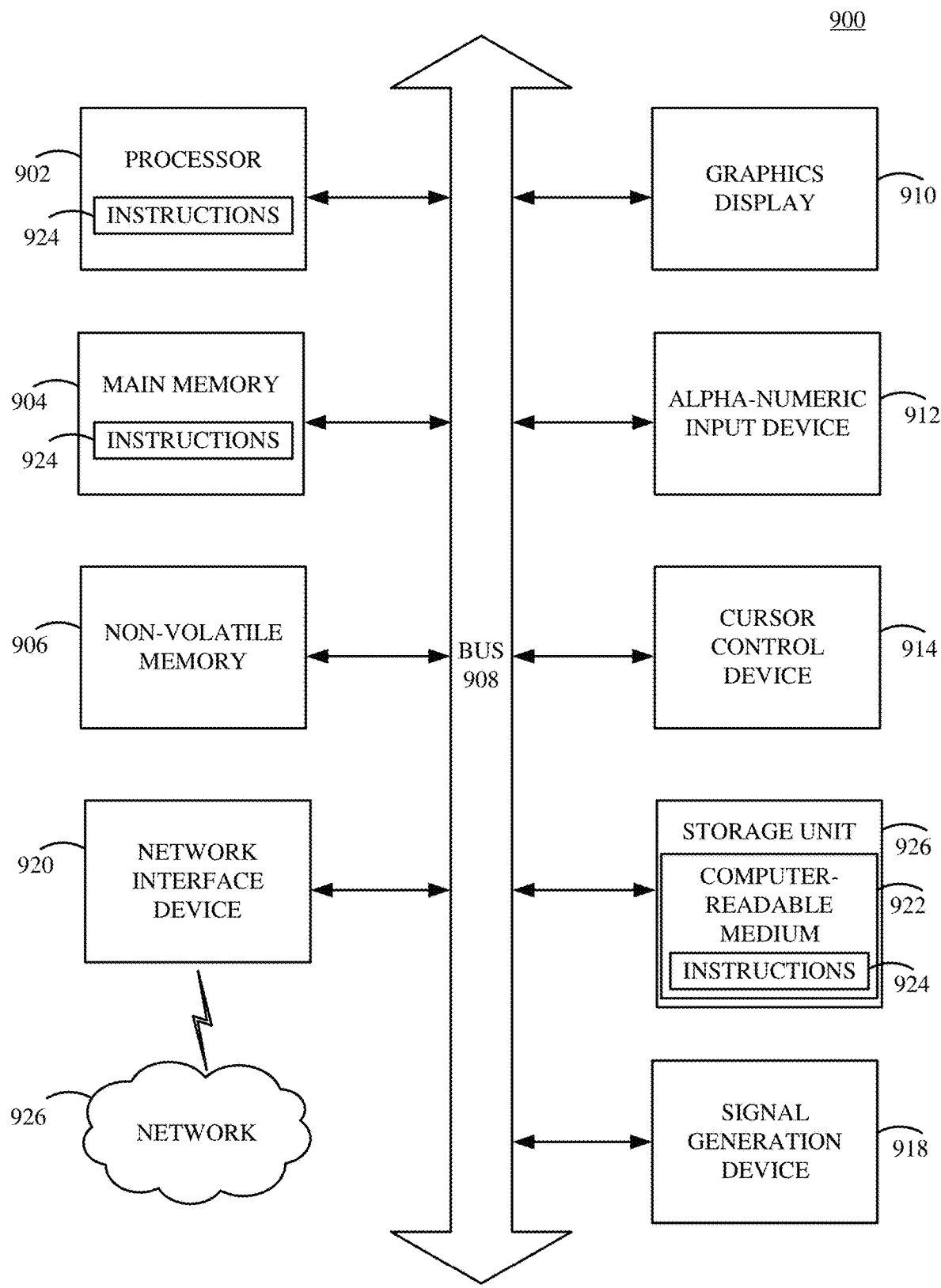
FIG. 9 is a block diagram illustrating components of example computing machines, in accordance with some embodiments.

FIG. 9 is a block diagram illustrating components of an example computing machine that is capable of reading instructions from a computer-readable medium and executing them in a processor (or controller). A computer described herein may include a single computing machine shown in FIG. 9, a virtual machine, a distributed computing system that includes multiples nodes of computing machines shown in FIG. 9, or any other suitable arrangement of computing devices.

By way of example, FIG. 9 shows a diagrammatic representation of a computing machine in the example form of a computer system 900 within which instructions 924 (e.g., software, program code, or machine code), which may be stored in a computer-readable medium for causing the machine to perform any one or more of the processes discussed herein may be executed. In some embodiments, the computing machine operates as a standalone device or may be connected (e.g., networked) to other machines. In a network deployment, the machine may operate in the capacity of a server machine or a client machine in a server-client network environment, or as a peer machine in a peer-to-peer (or distributed) network environment.

The structure of a computing machine described in FIG. 9 may correspond to any software, hardware, or combined components shown in FIG. 1, including but not limited to, the computing server 140, the local computer 120, the data store 130, the user device 170, and any computer that performs processes such as processes 600 and 700.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 924 that specify actions to be taken by that machine. Further, while only a single machine is illustrated, the term "machine" shall also be taken to include any collection of machines that individually or jointly execute instructions 924 to perform any one or more of the methodologies discussed herein.

The example computer system 900 includes one or more processors (generally, processor 902) (e.g., a central processing unit (CPU), a graphics processing unit (GPU), a digital signal processor (DSP), one or more application-specific integrated circuits (ASICs), one or more radio-frequency integrated circuits (RFICs), or any combination of these), a main memory 904, and a non-volatile memory 906, which are configured to communicate with each other via a bus 908. The computer system 900 may further include graphics display unit 910 (e.g., a plasma display panel (PDP), a liquid crystal display (LCD), a projector, or a cathode ray tube (CRT)). The computer system 900 may also include alphanumeric input device 912 (e.g., a keyboard), a cursor control device 914 (e.g., a mouse, a trackball, a joystick, a motion sensor, or other pointing instrument), a storage unit 916, a signal generation device 918 (e.g., a speaker), and a network interface device 920, which also are configured to communicate via the bus 908.

The storage unit 916 includes a computer-readable medium 922 on which is stored instructions 924 embodying any one or more of the methodologies or functions described herein. The instructions 924 may also reside, completely or at least partially, within the main memory 904 or within the processor 902 (e.g., within a processor's cache memory) during execution thereof by the computer system 900, the main memory 904 and the processor 902 also constituting computer-readable media. The instructions 924 may be transmitted or received over a network 926 via the network interface device 920.

While computer-readable medium 922 is shown in an example embodiment to be a single medium, the term "computer-readable medium" should be taken to include a single medium or multiple media (e.g., a centralized or distributed database, or associated caches and servers) able to store instructions (e.g., instructions 924). The computer-readable medium 922 may include any medium that is capable of storing instructions (e.g., instructions 924) for execution by the machine and that cause the machine to perform any one or more of the methodologies disclosed herein. The computer-readable medium 922 may include, but not be limited to, data repositories in the form of solid-state memories, optical media, and magnetic media. The computer-readable medium 922 does not include a transitory medium such as a signal or a carrier wave.

Example Use Cases

Patient Monitoring and Fall Prevention

The system described herein may be used in a hospital or other care facilities to monitor the motions of patients and prevent patients with limited mobility from falling or developing pressure injuries. By monitoring pressure data, the system may determine when a patient has been in the same position for longer than a predetermined threshold that indicates a risk of pressure injuries. A notification may be generated to alert the patient's caretaker that the position of the patient should be adjusted. The system may also determine when the patient is too close to the edge of the weight support device and alert the patent's caretaker that the patient is at the risk of falling. The system may also determine when there is significant fluctuation in the pressure data over a short period of time, which could suggest that the patient is having a seizure.

Infant/Toddler Monitoring

The system described herein may be used to monitor babies. Typically, baby monitors are video-based, and parents need to review videos recorded by the baby monitors to determine how the babies slept during the night. However, there may be privacy concerns for recording videos of the babies. With the virtual figure generated based on pressure data, parents can see how their babies moved without videos of the babies.

Sleep Therapy

The system described herein may be used to provide recommendations to improve sleep quality. The system may determine how a user moved while sleeping and determine a sleep quality score. For example, the system may determine how often the user woke up during the night, how frequently the user moved, whether the user was in an uncomfortable position, or other events that can affect the quality of the user's sleep. The system may also receive data from the user and make lifestyle adjustment recommendations for improving sleep quality. For example, the user may record exercise activity (e.g., type of exercise, time/duration of exercise), water consumption, and information on meals (e.g., types of meals, time of last meal before bed), and the system may determine how these factors affect the user's sleep quality. The system may be trained to provide recommendations for changing day time habits to improve sleep quality.

Posture Correction/Ergonomic Analysis

The system described herein may be used for posture correction or ergonomic analysis. The weight support device may be a chair (e.g., wheelchair, office chair, car seat) that users spend extended periods of time sitting in. Using pressure data, the system may determine when users are not sitting in proper posture that could lead to back or neck injuries. For example, the system may determine when the user's upper back is not making proper contact with pressure sensors installed at the back of the chair because the user is slouching or when the user's legs are not making proper contact with pressure sensors installed at the seat of the chair because the user is crossing their legs. The system may alert the user and make recommendations to get up and stretch or adjust their position to avoid injuries.

Additional Considerations

Beneficially, in some embodiments, the sleeping condition and poses of a user may be monitored using a support system throughout a sleeping cycle. The support system may be equipped with pressure sensors but can be implemented as a device that is similar to a regular mattress from the user perspective. In various embodiments, the one or more machine learning models used to predict the user's poses and positions and generate the virtual figure may be trained in a way that no additional monitoring device, such as a camera, is needed. As such, the sleeping condition of the user may be monitored in a least invasive setting without an installation of any additional device that could intrude the privacy of the user.

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Embodiments according to the invention are in particular disclosed in the attached claims directed to a method and a computer program product, wherein any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter which can be claimed comprises not only the combinations of features as set out in the disclosed embodiments but also any other combination of features from different embodiments. Various features mentioned in the different embodiments can be combined with explicit mentioning of such combination or arrangement in an example embodiment. Furthermore, any of the embodiments and features described or depicted herein can be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engine modules, without loss of generality. The described operations and their associated engine modules may be embodied in software, firmware, hardware, or any combinations thereof.

Any of the steps, operations, or processes described herein may be performed or implemented with one or more hardware or software engine modules, alone or in combination with other devices. In one embodiment, a software engine module is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure.

Throughout this specification, plural instances may implement components, operations, or structures described as a single instance. Although user operations of one or more methods are illustrated and described as separate operations, one or more of the user operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

The invention claimed is:

1. A system comprising:
a weight support device configured to support a user, wherein the user moves relative to the weight support device during a measurement period, the weight support device comprising a sensor grid including a plurality of sensors configured to measure pressure data; and
a computer comprising memory and one or more processors, the memory configured to store computer code comprising instructions, the instructions, when executed by the one or more processors, cause the one or more processors to:
generate a virtual figure that is a graphical representation of body parts of the user based on the pressure data, the virtual figure comprising discrete graphical representations including a torso representation, one or more limb representations, and a head representation, wherein the torso representation, the one or more limb representations, and the head representation are positioned relative to one another and respectively correspond to a torso, one or more limbs, and a head of the user measured by the pressure data at a given time during the measurement period;

define a plurality of key point locations of the user, wherein each key point location is a fixed reference point relative to a joint between the body parts of the user;

receive the pressure data from the plurality of sensors of the weight support device;

continuously track gradual changes in coordinates of the plurality of key point locations based on the pressure data;

determine that one or more key point locations are missing from the pressure data, indicating that a corresponding body part relative to one or more missing key point locations is not in contact with the weight support device;

apply a machine learning model to use a kinematic model to interpolate the coordinates of the one or more missing key point locations, the machine learning model is configured to interpolate the coordinates based on data related to natural posture of human, the coordinates of other detected key point locations, and constraints defined by human body joints;

adjust, based on the coordinates of the one or more missing key point locations, the virtual figure to change relative positions of the torso representation, the one or more limb representations, and the head representation, wherein the adjustment corresponds to movements of the user during the measurement period and shows a position of a discrete graphical representation corresponding to the at least one of the body parts that is not in contact with the weight support device; and output for display a presentation of changes in the relative positions of the torso representation, the one or more limb representations, and the head representation of the virtual figure.

2. The system of claim 1, wherein the virtual figure is a 3-dimensional figure representative of the user.

3. The system of claim 2, wherein the virtual figure is generated based on a height measurement and a weight measurement of the user.

4. The system of claim 1, wherein the torso representation and at least one limb representation of the virtual figure partially overlap.

5. The system of claim 1, wherein the instruction to generate the virtual figure comprises instructions to:
predict key point locations and a side of the user that is in contact with the weight support device based on the pressure data measured at the given time;
apply the kinematic model to the predicted key point locations and the predicted side, wherein the kinematic model is configured to determine the relative positions of the torso representation, the one or more limb representations, and the head representation of the virtual figure; and
generate the virtual figure based on the relative positions of the torso representation, the one or more limb representations, and the head representation of the virtual figure.

6. The system of claim 5, wherein the instruction to predict the key point locations comprises instructions to:
apply the pressure data to the machine learning model, the machine learning model trained using training data to predict a set of coordinates for each of the key point locations for each of a plurality of timestamps during the measurement period, wherein the training data includes historical entries that each includes pressure data and key point locations for historical users.

7. The system of claim 6, wherein a historical entry includes image data of a historical user annotated with key point locations.

8. The system of claim 7, wherein the machine learning model is configured to predict the set of coordinates for each of the key point locations without image data.

9. The system of claim 6, where the instruction to predict the key point locations comprises instructions to:
determine that a limb of the user is not in contact with the weight support device; and
predict one or more key point locations of the limb that is not in contact with the weight support device based on key point locations of at least one of another limb, the torso, and the head of the user that are in contact with the weight support device.

10. The system of claim 5, wherein the kinematic model is configured to predict a pose of the user based on the predicted key point locations and determine the relative positions of the torso representation, the one or more limb representations, and the head representation corresponding to the pose.

11. The system of claim 1, wherein a limb representation of a limb that is not in contact with the weight support device is visually distinguished relative to the torso representations, limb representations of limbs that are in contact with the weight support device, and the head representation.

12. The system of claim 1, wherein a video of the virtual figure representing the movement of the user during the measurement period is presented.

13. The system of claim 12, wherein the video is associated with an adjustable timeline, wherein responsive to receiving an interaction with the adjustable timeline specifying a timestamp, the display is updated to display the virtual figure representing a position of the user at the timestamp.

14. The system of claim 1, wherein the computer is further configured to predict a pressure injury outcome by:
inputting at least the pressure data collected by the weight support device into a second machine learning model, the machine learning model trained to predict a risk of the user developing pressure injury.

15. The system of claim 1, wherein at least one limb representation comprises segments connected by joints.

16. A computer-implemented method comprising:
receiving pressure data from a weight support device that comprises a sensor grid including a plurality of sensors that generates the pressure data, the pressure data associated with a user supported by the weight support device during a measurement period;
generating a virtual figure that is a graphical representation of body parts of the user based on the pressure data, the virtual figure comprising discrete graphical representations including a torso representation, one or more limb representations, and a head representation, wherein the torso representation, the one or more limb representations, and the head representation are positioned relative to one another and correspond to a torso, one or more limbs, and a head of the user measured by the pressure data at a given time during the measurement period;

defining a plurality of key point locations of the user, wherein each key point location is a fixed reference point relative to a joint between the body parts of the user;

receiving the pressure data from the plurality of sensors of the weight support device;

continuously tracking gradual changes in coordinates of the plurality of key point locations based on the pressure data;

determining that one or more key point locations are missing from the pressure data, indicating that a corresponding body part relative to one or more missing key point locations is not in contact with the weight support device;

applying a machine learning model to use a kinematic model to interpolate the coordinates of the one or more missing key point locations, the machine learning model is configured to interpolate the coordinates based on data related to natural posture of human, the coordinates of other detected key point locations, and constraints defined by human body joints;

adjusting, based on the coordinates of the one or more missing key point locations, the virtual figure to change relative positions of the torso representation, the one or more limb representations, and the head representation, wherein the adjustment corresponds to movements of the user during the measurement period and shows a position of a discrete graphical representation corresponding to the at least one of the body parts that is not in contact with the weight support device; and outputting for display a presentation of changes in the relative positions of the torso representation, the one or more limb representations, and the head representation of the virtual figure.

17. The computer-implemented method of claim 16, wherein the virtual figure is a 3-dimensional figure representative of the user.

18. The computer-implemented method of claim 16, wherein generating the virtual figure further comprises:
predicting key point locations and a side of the user that is in contact with the weight support device based on the pressure data measured at the given time;
applying the kinematic model to the predicted key point locations and the predicted side, wherein the kinematic model is configured to determine the relative positions of the torso representation, the one or more limb representations, and the head representation of the virtual figure; and
generating the virtual figure based on the relative positions of the torso representation, the one or more limb representations, and the head representation of the virtual figure.

19. The computer-implemented method of claim 18, wherein predicting the key point locations further comprises:
applying the pressure data to the machine learning model, the machine learning model trained using training data to predict coordinates for each of the key point locations for each of a plurality of timestamps during the measurement period, wherein the training data includes historical entries that each includes pressure data and key point locations for historical users.

20. The computer-implemented method of claim 19, wherein a historical entry includes image data of a historical user annotated with key point locations.

* * * * *